US011905561B2

(12) United States Patent
Al Mutairy et al.

(10) Patent No.: US 11,905,561 B2
(45) Date of Patent: Feb. 20, 2024

(54) METHOD FOR DIAGNOSING OR TREATING PULMONARY FIBROSIS USING S100A13 PROTEIN

(71) Applicant: KING FAISAL SPECIALIST HOSPITAL & RESEARCH CENTRE, Riyadh (SA)

(72) Inventors: Eid Abdullah Al Mutairy, Riyadh (SA); Mohammed Khalid, Riyadh (SA); Futwan Al-Mohanna, Riyadh (SA)

(73) Assignee: King Faisal Specialist Hospital & Research Centre, Riyadh (SA)

( * ) Notice: Subject to any disclaimer, the term of this patent is extended or adjusted under 35 U.S.C. 154(b) by 83 days.

(21) Appl. No.: 16/654,790

(22) Filed: Oct. 16, 2019

(65) Prior Publication Data

US 2020/0115427 A1 Apr. 16, 2020

Related U.S. Application Data

(60) Provisional application No. 62/746,058, filed on Oct. 16, 2018.

(51) Int. Cl.
| | |
|---|---|
| *C12Q 1/68* | (2018.01) |
| *C07H 21/04* | (2006.01) |
| *C12Q 1/6883* | (2018.01) |
| *A61P 9/00* | (2006.01) |
| *A61P 11/00* | (2006.01) |
| *C12Q 1/6827* | (2018.01) |
| *C07K 14/47* | (2006.01) |

(52) U.S. Cl.
CPC .............. *C12Q 1/6883* (2013.01); *A61P 9/00* (2018.01); *A61P 11/00* (2018.01); *C12Q 1/6827* (2013.01); *C07K 14/47* (2013.01); *C07K 14/4728* (2013.01)

(58) Field of Classification Search
None
See application file for complete search history.

(56) References Cited

U.S. PATENT DOCUMENTS

| | | |
|---|---|---|
| 2003/0065157 A1 | 4/2003 | Lasek |
| 2003/0198970 A1 | 10/2003 | Roberts |
| 2011/0312922 A1 | 12/2011 | Fagerhol et al. |
| 2012/0053062 A1* | 3/2012 | Brooks ................ C12Q 1/6883 506/2 |
| 2012/0225954 A1* | 9/2012 | Moran .................... A61P 35/00 514/789 |
| 2015/0086510 A1 | 3/2015 | Gauglitz et al. |

FOREIGN PATENT DOCUMENTS

| | | |
|---|---|---|
| EP | 1 169 441 B1 | 6/2005 |
| WO | 2016/172710 A2 | 10/2016 |

OTHER PUBLICATIONS

Morlan et al. Mutation Detection by Real-Time PCR: A Simple, Robust and Highly Selective Method. PLOS ONE; 2009; 4; 2; e4584: p. 1-11. (Year: 2009).*
Balestri et al. Nine differentially expressed genes from a post mortem study and their association with suicidal status in a sample of suicide completers, attempters and controls. Journal of Psychiatric Research; 2017; 91: 98-104. (Year: 2017).*
Cao et al. Effect of Human S100A13 Gene Silencing on FGF-1 Transportation in Human Endothelial Cells. J Formos Med Assoc; 2010; 109(9): 632-640. (Year: 2010).*
Brennan and Schrijver. Cystic Fibrosis: A Review of Associated Phenotypes, Use of Molecular Diagnostic Approaches, Genetic Characteristics, Progress, and Dilemmas. The Journal of Molecular Diagnostics; 2016; 18; 1: 3-14. (Year: 2016).*
Putman et al. Genetics and Early Detection in Idiopathic Pulmonary Fibrosis. American Journal of Respiratory and Critical Care Medicine; 2014; 189; 7: 770-778. (Year: 2014).*
Gracia et al. Genotype-phenotype correlation for pulmonary function in cystic fibrosis. Thorax 2005; 60: 558-563. (Year: 2005).*
Landriscina et al. S100A13, a new marker of angiogenesis in human astrocytic gliomas. J Neurooncol; 2006; 80:251-259. (Year: 2006).*
Aloi et al. Wolfram Syndrome: New Mutations, Different Phenotype. PLOS ONE: 2012; 7; 1: e29150: p. 1-6. (Year: 2012).*
Henderson et al. Fibrosis: from mechanisms to medicines. Nature; 2020; vol. 587; 26: 555-566 (Review). (Year: 2020).*
Henderson et al. Nature; 2020; vol. 587; 26: 555-566. (Year: 2020).*
Mayo Clinic, Pulmonary Fibrosis, https://www.mayoclinic.org/diseases-conditions/pulmonary-fibrosis/diagnosis-treatment/drc-20353695, Jan. 2023 (Year: 2023).*
Boni et al. (British Journal of Dermatology; vol. 137:39-43 1997) (Year: 1997).*
Al-Mutairy et al. (Eur Respir J., vol. 54, No. 1, Jul. 18, 2019). (Year: 2019).*
Wicki et al. (Biochemical and Biophysical Research Communications, vol. 227, pp. 594-599, 1996). (Year: 1996).*
Kiener et al. (Front. Med. Review Article, May 7, 2021, vol. 8, Article 644678, Human-based Advanced in vitro approaches to investigate lung fibrosis and pulmonary effects of COVID-19 (Year: 2021).*
Jenkins et al. (Am. J. of Respiratory Cell and Molecular Biology, vol. 56, No. 5, 2017) (Year: 2017).*
XM 001724603 Genbank Entry , 2008 (Year: 2008).*
Pierce, et al. ; Identification of a novel, functional role for S100A13 in invasive lung cancer cell lines ; European Journal of Cancer 44 ; pp. 151-159 ; Oct. 9, 2007 ; 9 Pages.

* cited by examiner

*Primary Examiner* — Jeanine A Goldberg
(74) *Attorney, Agent, or Firm* — Oblon, McClelland, Maier & Neustadt, L.L.P.

(57) ABSTRACT

The invention is directed to a method for diagnosing and treating fibrosis, especially pulmonary fibrosis, associated with mutation of the S100A13 and S100A3 genes. Methods for detecting and distinguishing the mutant forms of these genes are disclosed and ways to compensate for loss of function or aberrant function of the mutated S100A13 or S100A3 proteins are disclosed.

14 Claims, 25 Drawing Sheets

Specification includes a Sequence Listing.

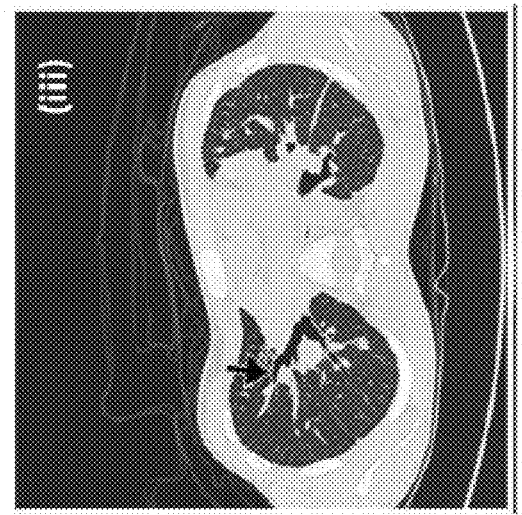
FIG. 1A  FIG. 1B  FIG. 1C
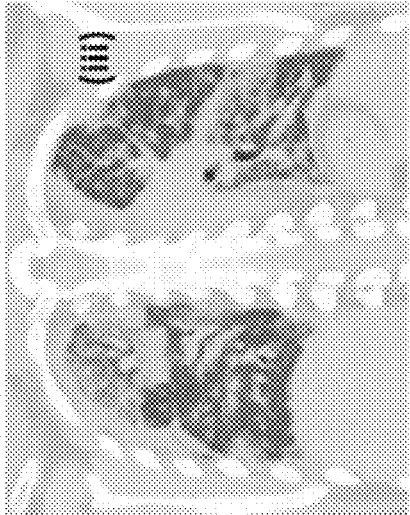
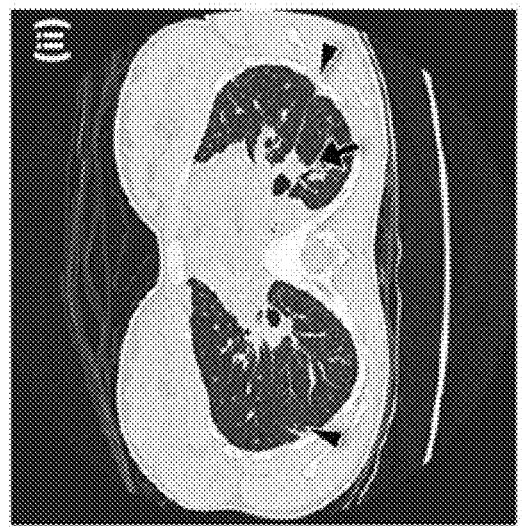
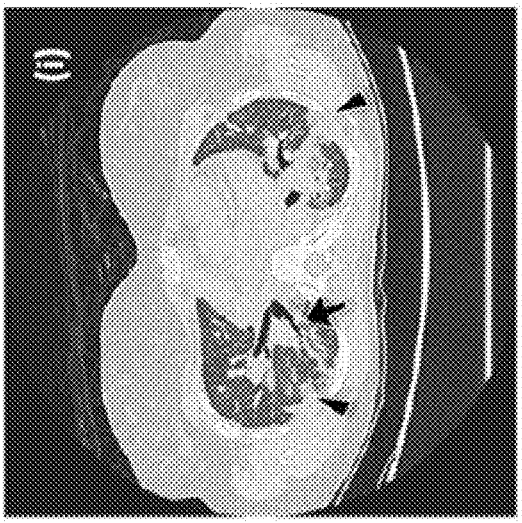

FIG. 1G
| | FVC [L] (% predicted) | FEV1 [L] (% predicted) | Ratio (FEV1/FVC) | TLC [L] (% predicted) |
|---|---|---|---|---|
| Subject 1 | 0.39 (11%) | 0.36 (12%) | 91 | 1.43 (31%) |
| Subject 2 | 0.51 (15%) | 0.51 (17%) | 100 | 1.31 (28%) |
| Subject 3 | 0.87 (16%) | 0.84 (19%) | 96 | 2.24 (19%) |
| Carrier Mother | 2.58 (86%) | 2.0 (80%) | 77 | 4.22 (90%) |
| Carrier Brother | 3.64 (83%) | 3.27 (90%) | 89 | 4.5 (81%) |
FVC= Forced vital capacity; FEV1= Forced expiratory volume in 1 second; TLC=Total Lung Capacity
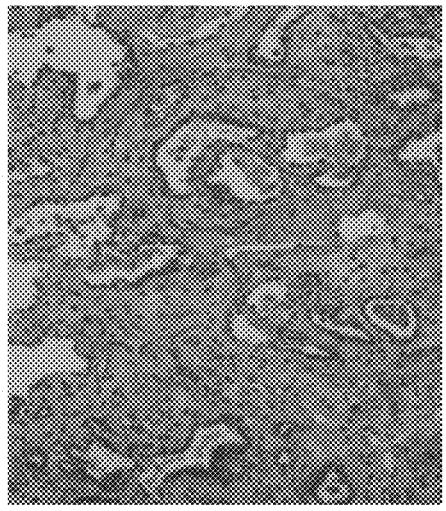
FIG. 1H
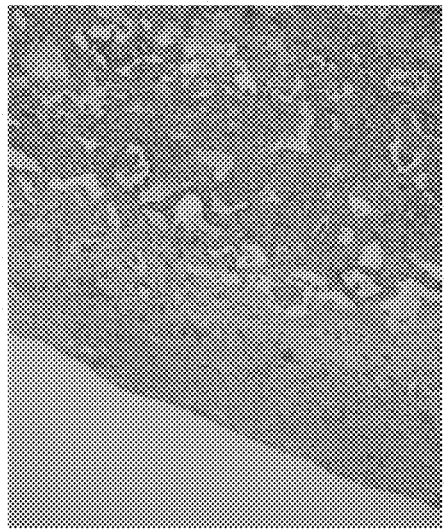
FIG. 1I
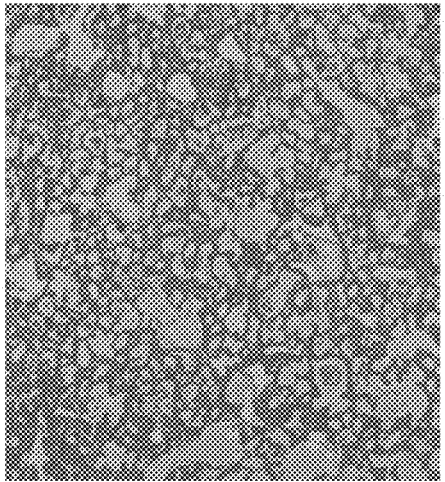
FIG. 1J

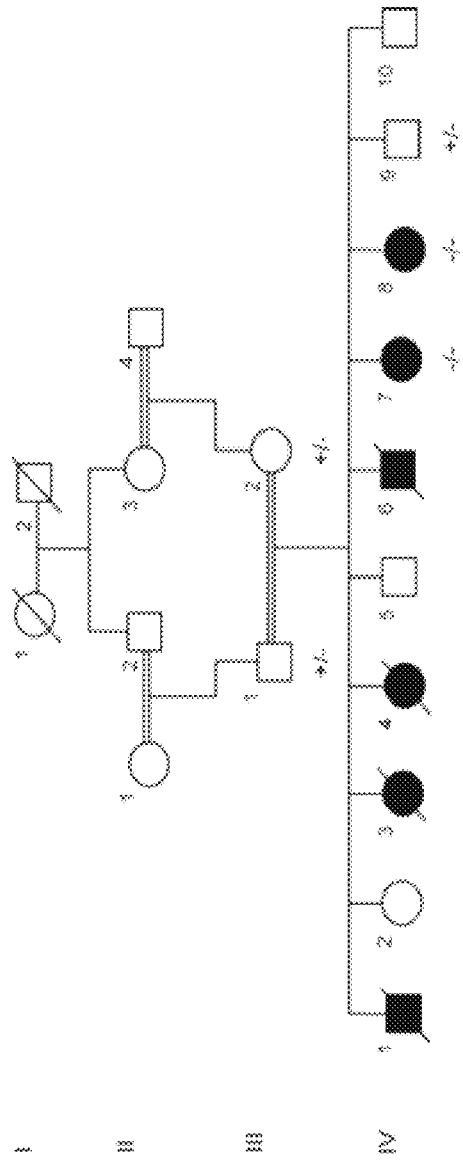

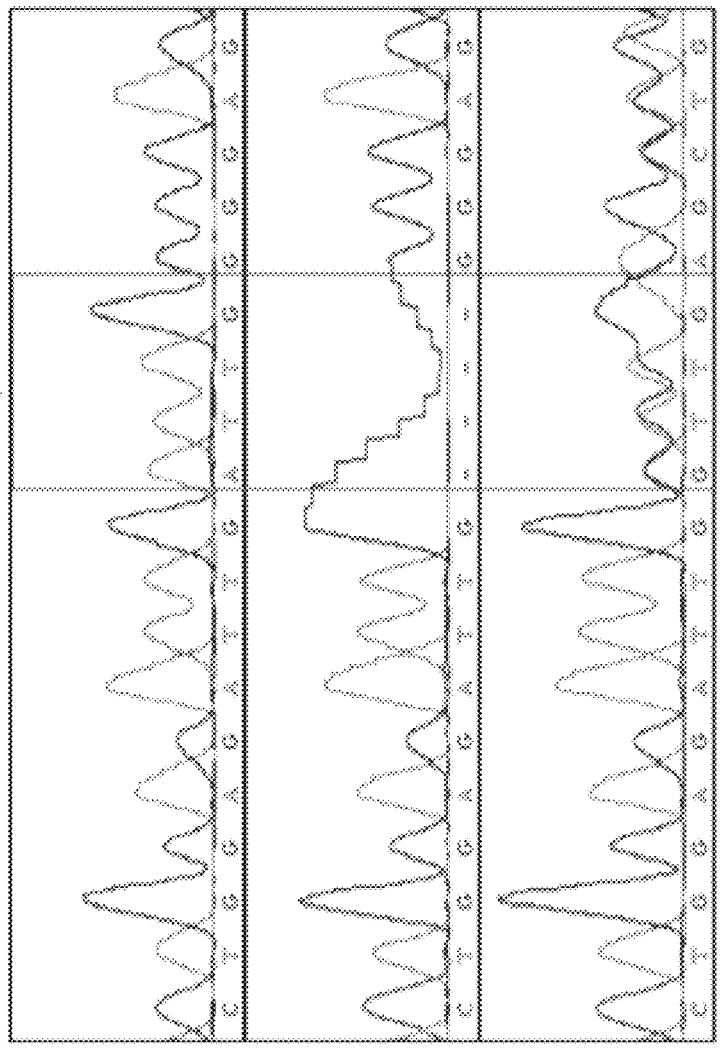
FIG. 2F Normal wild type
FIG. 2G Homozygous affected
FIG. 2H Heterozygous carrier Normal wild type Homozygous affected Heterozygous carrier

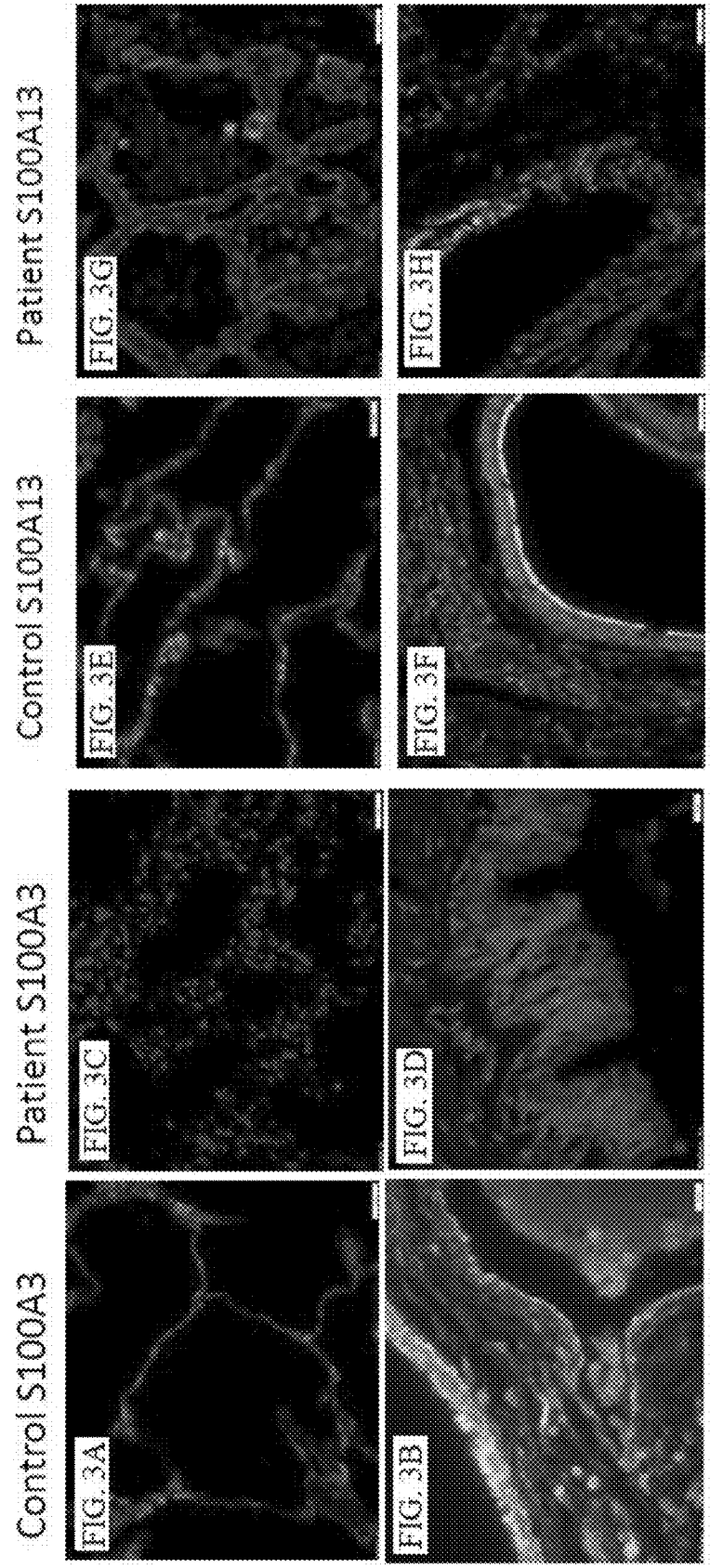

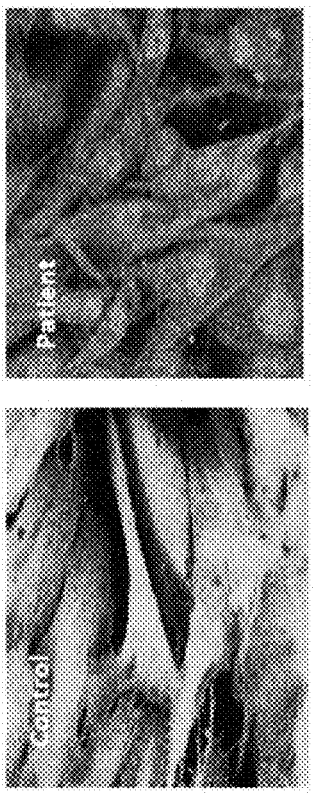
FIG. 3O
FIG. 3N
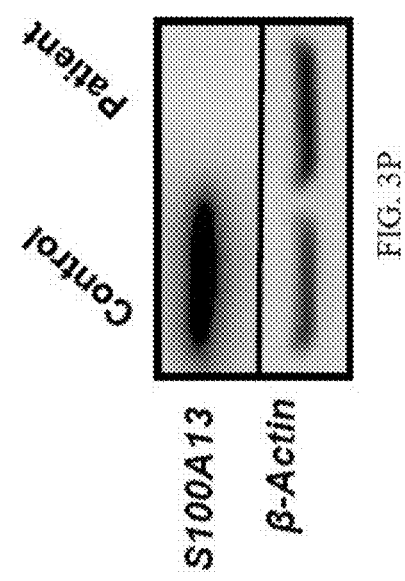
FIG. 3P
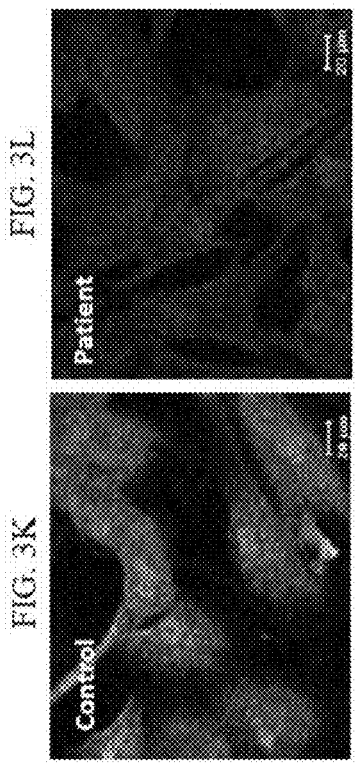
FIG. 3L
FIG. 3K
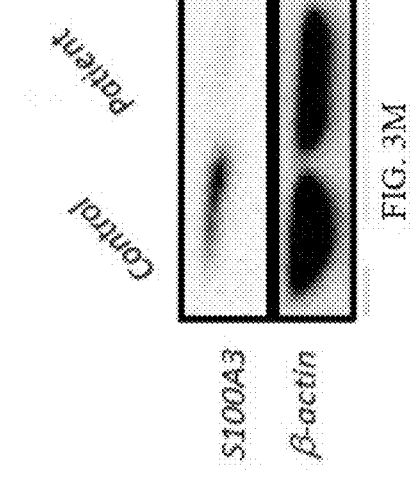
FIG. 3M

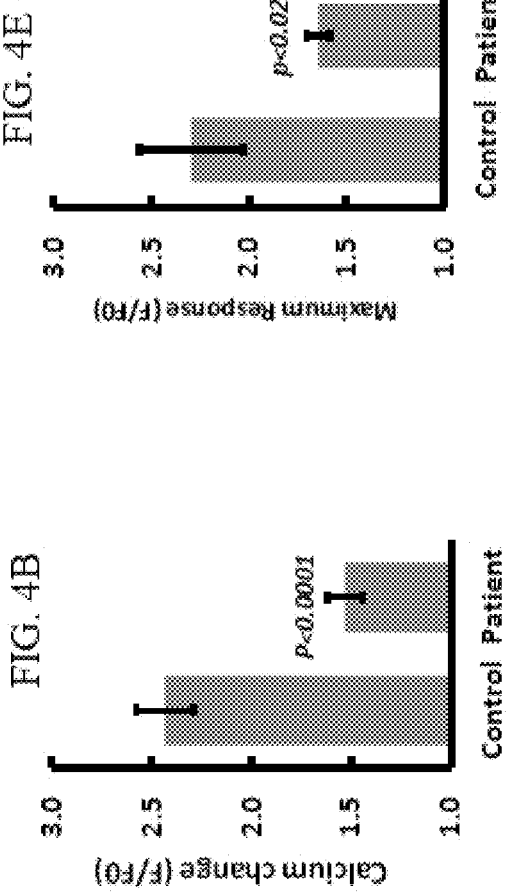
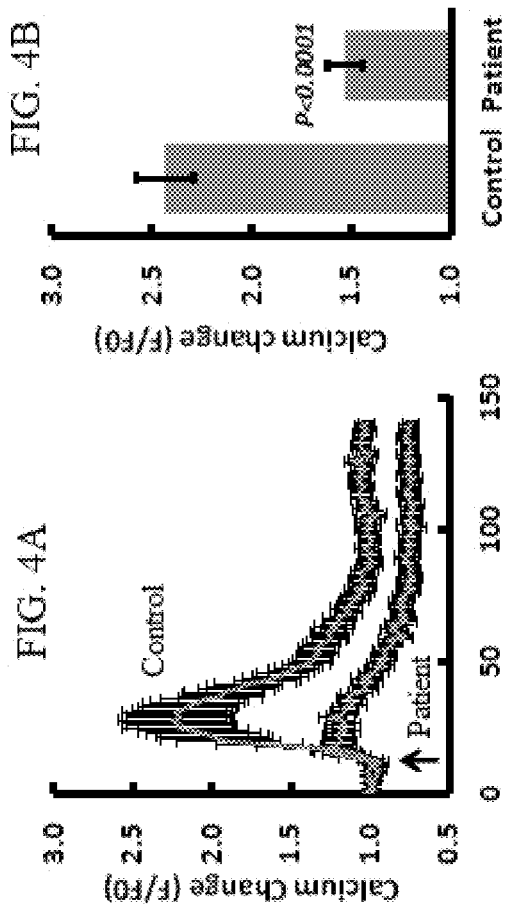
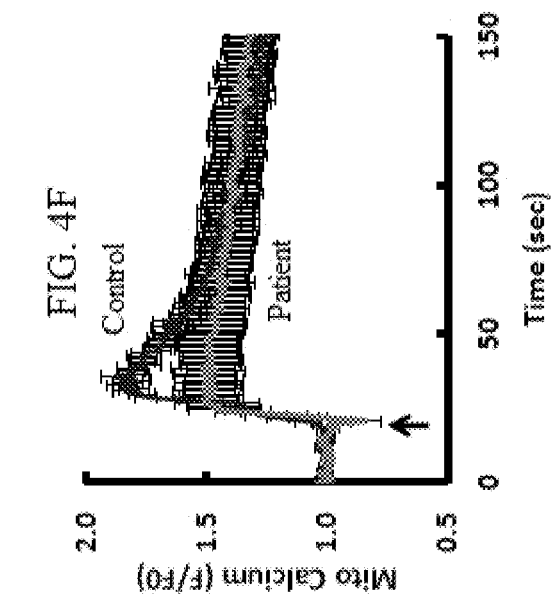
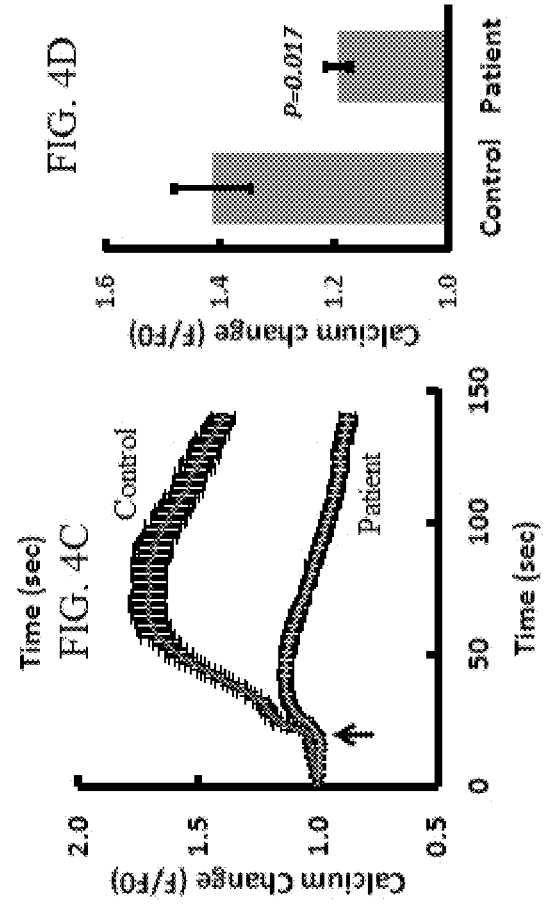

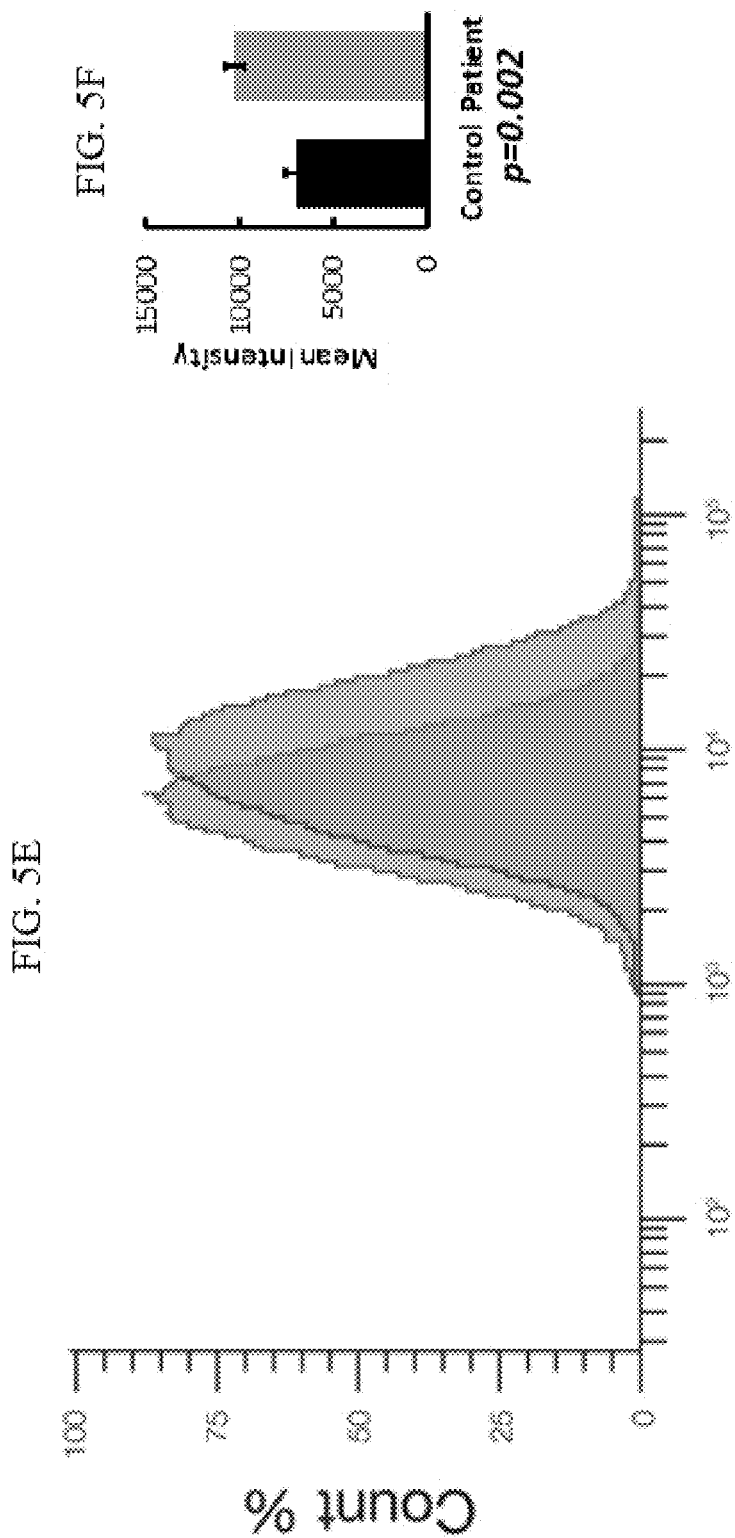

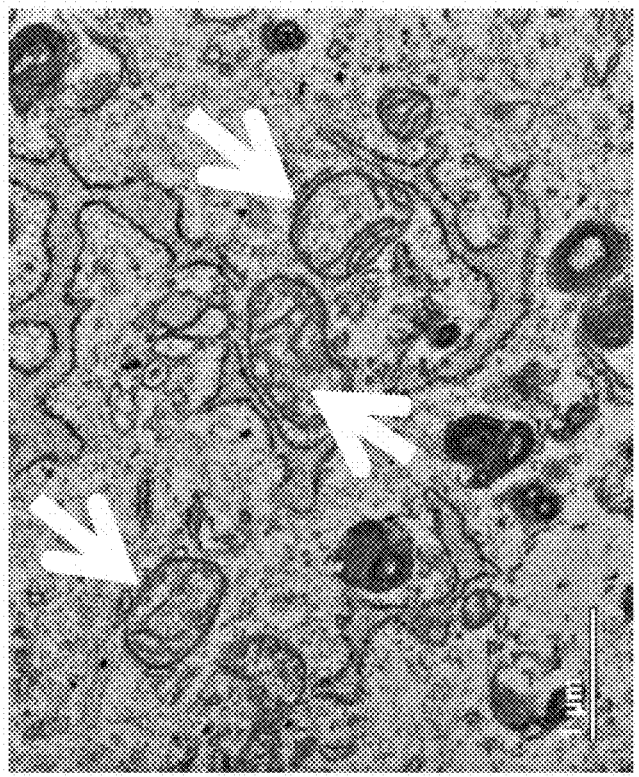

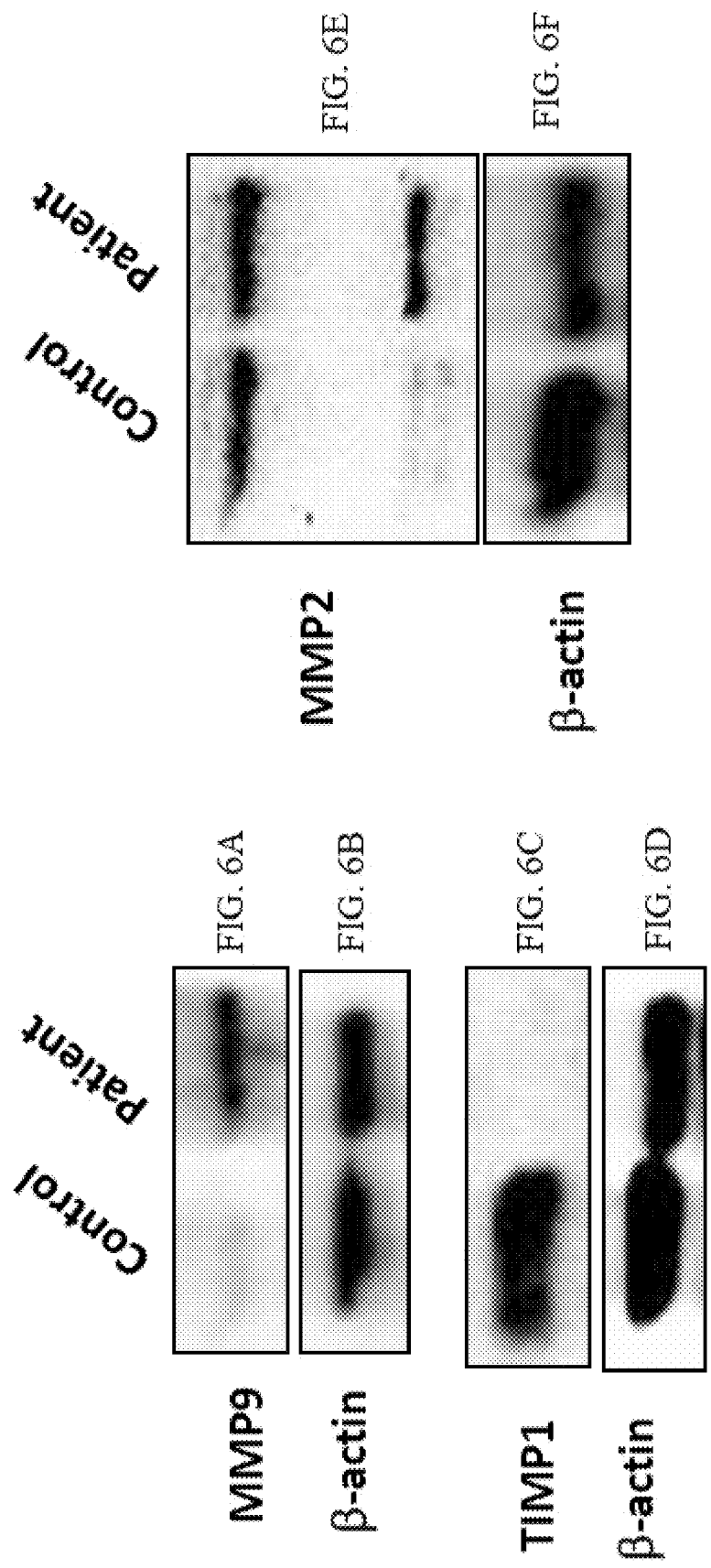

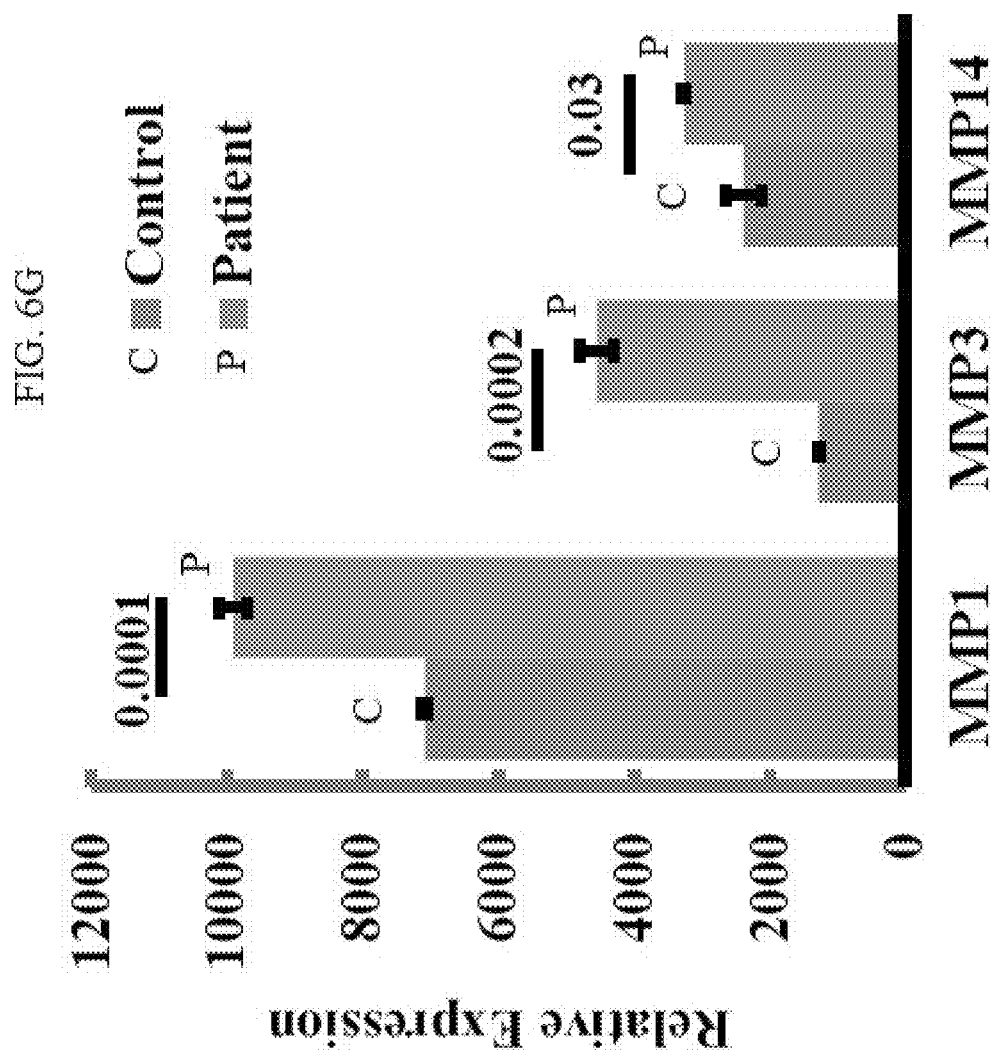

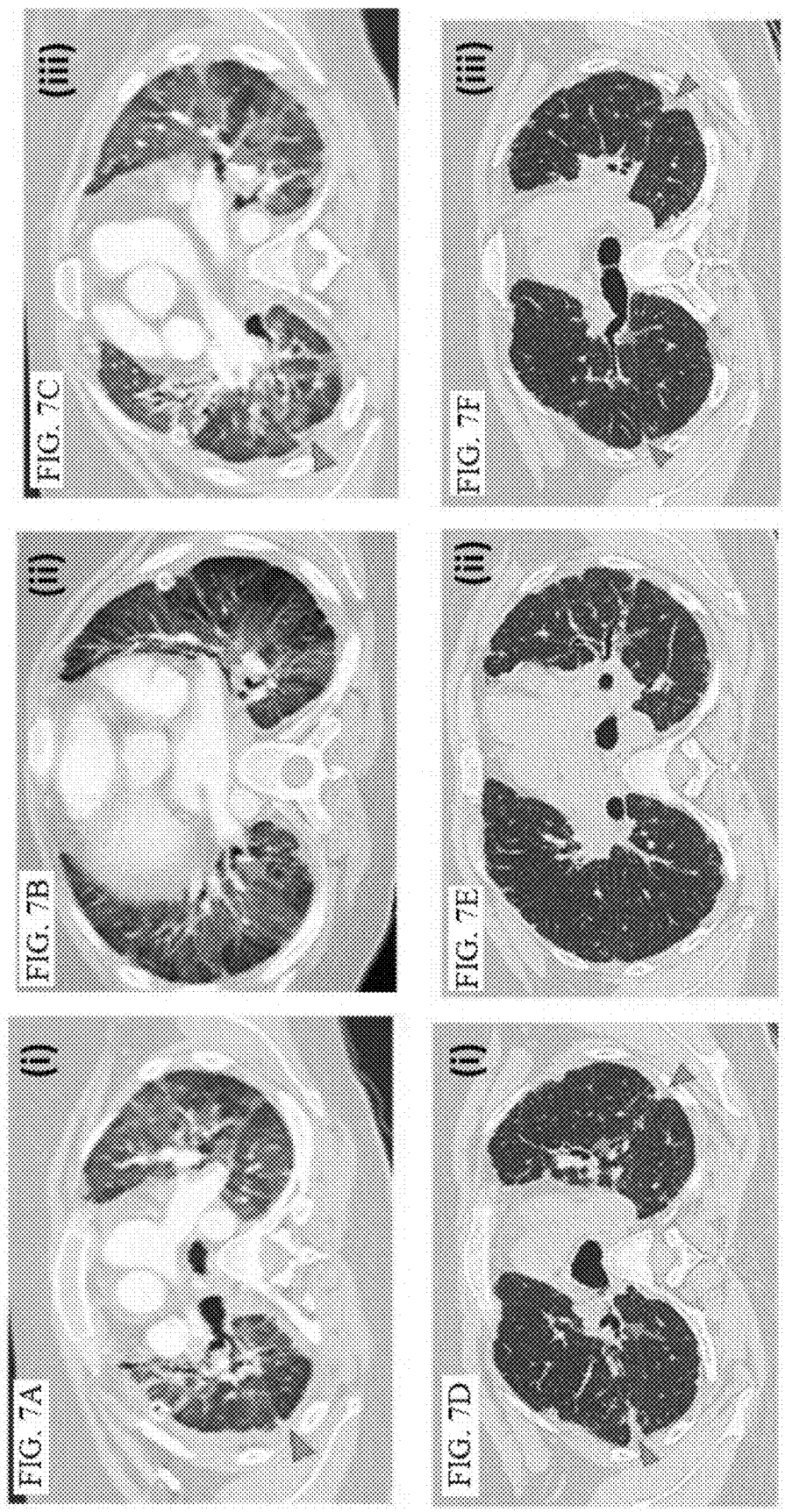

FIG. 7G
| | FVC [L] (%Predicted) | FEV1 [L] (%Predicted) | Ratio (FEV1/FVC) | TLC [L](%Predicted) |
|---|---|---|---|---|
| Subject 1 | 0.54 (14.4%) | 0.52 (5.9%) | 97.77% | 2.16 (41.8%) |
| Subject 2 | 1.05 (30%) | 0.88 (30%) | 84% | 1.85 (36%) |
FVC=Forced vital capacity; FEV1=Forced expiratory volume in 1 second; TLC=Total Lung Capacity
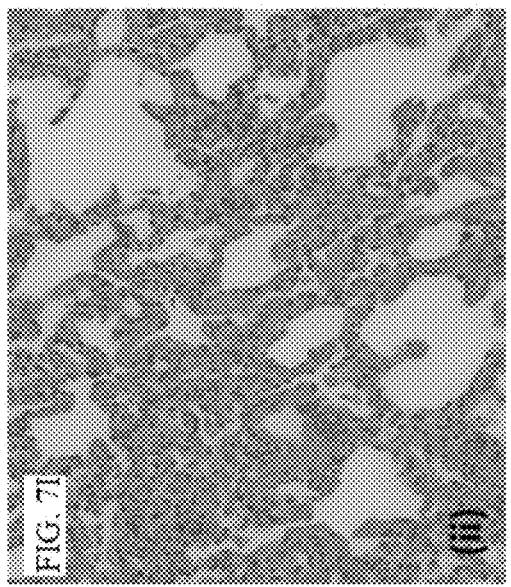
FIG. 7I
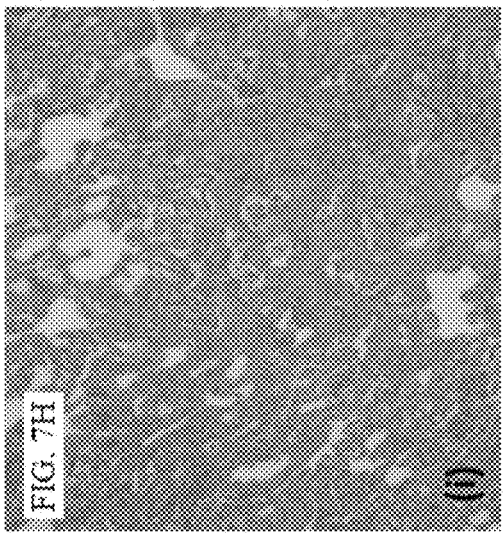
FIG. 7H

METHOD FOR DIAGNOSING OR TREATING PULMONARY FIBROSIS USING S100A13 PROTEIN

CROSS-REFERENCE TO RELATED APPLICATIONS

This application claims priority to U.S. Provisional Application No. 62/746,058, filed Oct. 16, 2018 which is incorporated by reference in its entirety.

REFERENCE TO A SEQUENCE LISTING

In accordance with 37 CFR § 1.52(e)(5), the present specification makes reference to a Sequence Listing submitted electronically as a .txt file named "517595US_ST25.txt" on Oct. 16, 2019. The .txt file was generated on Oct. 10, 2019 and is 16.8 kb in size. The entire contents of the Sequence Listing are herein incorporated by reference.

BACKGROUND

Field of the Invention

The invention involves the fields of diagnostic and therapeutic genetic medicine especially to diagnostic and therapeutic methods involving S100A13 or a combination of S100A13 and S100A3.

Description of Related Art

The "background" description provided herein is for the purpose of generally presenting a context for the disclosure. Work of the presently named inventor(s), to the extent it is described in this background section, as well as aspects of the description which may not otherwise qualify as prior art at the time of filing, are neither expressly or impliedly admitted as prior art against the present invention.

The Interstitial Lung Diseases (ILDs) are a heterogeneous group of disorders of largely unknown etiology. They are characterized by variable types of interstitial and alveolar inflammation, parenchymal remodeling, and fibrosis; Nogee L M. *Genetics of pediatric interstitial lung disease*. Current opinion in pediatrics 2006; 18:287-92—incorporated herein by reference. The most common form of ILD is idiopathic Pulmonary Fibrosis (IPF), a progressive disorder that usually affects individuals over 55 years of age and is histopathologically manifested by the Usual Interstitial Pneumonitis (UIP) pattern characterized by variable degrees of inflammation, honeycomb cysts, distortion of the lung architecture, fibroblastic foci, fibrosis, and marked spatial heterogeneity; Raghu G, Collard H R, Egan J J, et al. *An official ATS/ERS/JRS/ALAT statement: idiopathic pulmonary fibrosis: evidence-based guidelines for diagnosis and management*. American journal of respiratory and critical care medicine 2011; 183:788-824—incorporated herein by reference. Because of the lack of effective treatments and the rapid progression to respiratory failure and death, IPF remains one of the leading indications for lung transplantations worldwide; Rahu, et al., id.; Yusen R D, Christie J D, Edwards L B, et al. *The Registry of the International Society for Heart and Lung Transplantation: Thirtieth Adult Lung and Heart-Lung Transplant Report—2013; focus theme: age*. The Journal of heart and lung transplantation: the official publication of the International Society for Heart Transplantation 2013; 32:965-78. Several environmental risk factors have been implicated in the pathogenesis of IPF including cigarette smoking and chronic aspiration (Rahu, et al., id), and a genetic predisposition has been demonstrated (Marshall R P, McAnulty R J, Laurent G J. *The pathogenesis of pulmonary fibrosis: is there a fibrosis gene?* The International Journal of Biochemistry & Cell Biology 1997; 29:107-20), however, the great majority of cases of IPF are sporadic.

The pathogenesis of IPF remains poorly understood and progress is hindered by the lack of an animal model that recapitulates the salient features of the human disease. Recently identified kindred with ILD developing in multiple members have provided potential clues to the pathogenesis of IPF occurring in the general population; Kropski J A, Lawson W E, Young L R, Blackwell T S. *Genetic studies provide clues on the pathogenesis of idiopathic pulmonary fibrosis*. Disease models & mechanisms 2013; 6:9-17.

Familial Pulmonary Fibrosis (FPF), defined as idiopathic interstitial lung disease in two or more first-degree relatives (parent, sibling, or offspring), has been attributed to non-synonymous mutations in surfactant protein A2 (SFTPA2), surfactant protein C (SFTPC) and ATP-binding cassette A3 (ABCA3)(Lawson W E, Grant S W, Ambrosini V, et al. *Genetic mutations in surfactant protein C are a rare cause of sporadic cases of IPF*. Thorax 2004; 59:977-80; Wang Y, Kuan P J, Xing C, et al. *Genetic defects in surfactant protein A2 are associated with pulmonary fibrosis and lung cancer*. American Journal of Human Genetics 2009; 84:52-9), and to a common variant in the promoter of the gene encoding mucin 5B (MUC5B) that increases MUC5B expression by 37.4-fold; Seibold M A, Wise A L, Speer M C, et al. *A common MUC5B promoter polymorphism and pulmonary fibrosis*. The New England Journal of Medicine 2011; 364:1503-12.

These mutations are proposed to converge on activation of the unfolded protein response; Kropski, J A, et al., 2013, id. A plurality of FPF kindreds, ~15%, have mutations in the telomerase genes, TERT and TERC, and exhibit shortened telomeres; Tsakiri K D, Cronkhite J T, Kuan P J, et al. *Adult-onset pulmonary fibrosis caused by mutations in telomerase*. Proceedings of the National Academy of Sciences of the United States of America 2007; 104:7552-7; Armanios M Y, Chen J J, Cogan J D, et al. *Telomerase mutations in families with idiopathic pulmonary fibrosis*. The New England Journal of Medicine 2007; 356:1317-26.

Telomere shortening is also evident in 25% of patients with sporadic IPF who do not have identifiable mutations in TERT or TERC; Cronkhite J T, Xing C, Raghu G, et al. *Telomere shortening in familial and sporadic pulmonary fibrosis*. American Journal of Respiratory and Critical Care Medicine 2008; 178:729-37. Despite these advances, the pathogenesis of sporadic IPF remains unclear.

Accordingly it is one object of the present disclosure to identify and describe new protein mutations and/or genetic mutations associated with pulmonary fibrosis and to use them to identify, treat and characterize pulmonary fibrosis.

BRIEF SUMMARY OF THE INVENTION

As shown herein the inventors identified two variant genes encoding calcium binding proteins which segregated in seven and two siblings screened from two unrelated families with pulmonary fibrosis (PF). These genes are S100A13 (NM 002960) and S100A3 (NM 002960). The mutation in S100A3 comprises c.229C>T and encodes a protein comprising p.R77C), see SEQ ID NOS: 3 and 4. The mutation in S100A13 comprises c.238-241delATTG and encodes a protein comprising the frameshift p.I80Gfs*13, see SEQ ID NOS: 15 and 16.

The mutations lead to lower expression of the S100A3 and S100A13 proteins and are associated with aberrant intracellular calcium homeostasis, reduced capacity to tolerate oxidative stress, and altered extracellular matrix ("ECM") protein expression in cells isolated from the patients.

Indirect immunofluorescence and Western blots demonstrated decreased expression of the mutant S100A13 and S100A3 proteins in the lungs of patients and in cells isolated from the patient's skin. This was concomitant with aberrant calcium homeostasis in isolated patient's fibroblasts. The introduction of wild type gene in the patient's cells restored their normal calcium responses. Furthermore, the introduction of the mutant transcript caused aberrant calcium homeostasis that was similar to that of seen in patient's cells.

These results indicate that S100A13 and/or S100A3 regulate pulmonary fibrosis and restoration of S100A13 protein levels may reverse the clinical symptoms and provide a new therapy for the disease. It is a further object of the present disclosure to provide a method for predicting risk of fibrosis and mitigating and/or reducing this risk or treating fibrosis associated with these mutant genes.

Embodiments of the invention include but are not limited to the following.

One embodiment of the invention is a method for determining a risk of fibrosis, especially pulmonary fibrosis, comprising detecting a mutant S100A13 and/or S100A3 polynucleotide or a mutant S100A13 or mutant S100A3 protein in a biological sample from a subject; selecting a subject at increased risk of fibrosis when said mutant S100A13 and/or S100A3 polynucleotide or said mutant S100A13 and/or S100A3 protein is detected; and treating the subject to reduce a risk of fibrosis or to ameliorate fibrosis. Typically, a mutant S100A13 or S100A3 protein will lack one or more functions of the corresponding wild-type protein or have diminished functional activity compared to the wild-type protein, such as no more than 95, 90, 80, 70, 60, 50, 40, 30, 20, 10, 5 or <5% of the corresponding functional activity of the wild-type protein. Functions of the S100A13 and S100A3 proteins include, but are not limited to regulation of intracellular calcium homeostasis, regulation of oxidative stress, maintaining normal expression levels of extracellular matrix ("ECM") proteins. Normal values are those, for example, associated with the functional S100A13 and S100A3 proteins described by SEQ ID NOS: 2 and 14.

In some embodiments, the mutant polynucleotide encoding S100A13 will have a sequence that differs from that of wild-type S100A13 which is described by the wild-type sequence of SEQ ID NO: 13 and a mutant S100A13 protein will have a sequence that differs from that of the wild-type sequence of SEQ ID NO: 14.

In some embodiments the mutant S100A13 polynucleotide comprises the deletion c.238-241delATTG to the wild-type polynucleotide sequence of SEQ ID NO: 13. In one specific embodiment, the mutant polynucleotide comprises the polynucleotide sequence described by SEQ ID NO: 15 and the mutant S100A13 protein comprises the amino acid sequence of SEQ ID NO: 16. Other S100A13 mutants may have mutations to the same domain(s) or segment(s) of the wild-type proteins as this S100A13 mutant.

In some embodiments, the mutant polynucleotide encoding S100A3 will have a sequence that differs from that of wild-type S100A3 which is described by SEQ ID NO: 1, for example, the mutant S100A3 polynucleotide may comprise a substitution mutation 229C>T to the wild-type polynucleotide sequence described by SEQ ID NO: 1. Other S10013 mutants may have mutations to the same domain or segment of the wild-type protein as this S100A3 mutant.

A mutant S100A3 protein will have a sequence that differs from that of wild-type sequence of SEQ ID NO: 2. For example, the mutant S100A3 protein may have a substitution at residue 77 replacing arginine with another amino acid residue, such as with cysteine.

In the method disclosed herein, the mutant S100A13 or S100A3 polynucleotide can be detected using probes and/or primers that specifically bind to or amplify a mutated segment of the mutant S100A13 or S100A3 polynucleotide. Primers that amplify a polynucleotide encoding a mutant S100A13 or S100A3 protein may be designed by methods known in the art, such as those disclosed by Primer-BLAST available at hypertext transfer protocol secure://_www.ncbi.nlm.nih.gov/tools/primer-blast) (incorporated herein by reference, last accessed on Jul. 1, 2019). Primers and probes that identify polynucleotides encoding mutant S100A3 proteins may also be designed using tools such as OligoArchitect™ tool available from Sigma-Aldrich which are incorporated by reference to hypertext transfer protocol secure://_www.sigmaaldrich.com/technical-documents/articles/biology/oligoarchitect-online.html (last accessed on Jul. 1, 2019). Those skilled in the art can design primers and probes for amplification and/or detection of polynucleotides encoding S100A13 or S100A3 mutant polypeptides using these tools and then select primers that preferentially amplify or hybridize to polynucleotides encoding mutant S100A13 or mutant S100A3 protein in comparison to those encoding the wild-type S100A13 or S100A3 protein. In one embodiment of the primers or probes of the invention will identify or amplify the frameshift mutation in the mutant S100A13 gene of SEQ ID NO: 15 or the c.229C>T substitution as shown in SEQ ID NO: 3.

In other embodiments of the method disclosed herein, the mutant S100A13 or S100A3 protein is detected using antibodies that specifically bind to a mutated segment or epitope of the mutant S100A13 or S100A3 protein.

An antibody to a mutant S100A13 protein, such as one that binds to mutant S100A13 (SEQ ID NO: 16) carrying the frameshift mutation or an antibody to a mutant S100A3 protein containing the p.R77C mutation (SEQ ID NO: 4) will preferably have a higher affinity or avidity for the mutant S100A13 protein or mutant S100A3 protein than for the corresponding wild-type protein, more preferably, it will bind to the mutant S100A13 or mutant S100A3 protein but will not substantially bind to the respective corresponding wild-type S100A13 or S100A3 proteins such as the wild-type proteins described by SEQ ID NOS: 2 and 14. Linear B cell epitopes of a mutant S100A13 or mutant S100A3 protein will typically contain one or more mutations to the wild-type amino acid sequence, such as deletions, insertions, or substitutions to 1, 2, 3, 4, 5, 6, 7, 8, 9 or 10 amino acid residues.

B cell epitopes typically contain about 5 to 20 amino acid residues Those skilled in the art can identify B cell epitopes of S100A13 and S100A3 wild-type or mutant proteins by methods known in the art including those described by El-Manzalawy Y, et al., Comput Syst Bioinformatics Conf. 2008; 7: 121-132.

A B cell epitope on a mutant S100A3 protein may span 5, 6, 7, 8, 9, 10, 11, 12, 13, 14, 15, 16, 17, 18, 19 or 20 amino acid residues of SEQ ID NO: 4 and contain the p.R77C mutation or another mutation to residue 77 (or other residues) of wild-type S100A3 protein.

A B cell epitope on a mutant S100A13 protein may span 5, 6, 7, 8, 9, 10, 11, 12, 13, 14, 15, 16, 17, 18, 19 or 20 amino acid residues of SEQ ID NO: 16 and contain the frameshift mutation that distinguishes this sequence from the wild-type sequence of SEQ ID NO: 14.

Mutant S100A13 or S100A3 proteins and their peptide fragments having B cell epitopes may be used to produce polyclonal or monoclonal antibodies by methods known in the art including those described by or cited to by hypertext transfer protocol secure://_en.wikipedia.org/wiki/Monoclonal_antibody (incorporated by reference, last accessed Jul. 1, 2019).

In some instances, a mutation will be part of, of form by its allosteric effects, a conformational epitope that can be used to distinguish a mutant S100A13 or mutant S100A3 protein from the corresponding wild-type S100A13 or S100A3 protein.

In a further embodiment of the method as disclosed herein, the method determines whether the subject is normal and has two wild-type S100A13 and/or S100A3 genes, or homozygous or heterozygous for the mutant S100A13 and/or S100A3 polynucleotide or S100A13 and S100A3 polynucleotides, wherein a subject who is homozygous for the mutant S100A13 or mutant S100A3 polynucleotide is selected to be at higher risk of fibrosis than a subject who is heterozygous for the mutant S100A13 or S100A3 polynucleotide, who is at higher risk for fibrosis than a subject who is homozygous for wild-type S100A13 or wild-type S100A3 polynucleotides. For example, primers or probes that specifically recognize the wild-type and mutant forms of S100A13 or S100A3 may be used for this purpose, or antibodies that distinguish between wild-type and mutant forms of the S100A13 and S100A3 may be used. In some embodiments, the method may involve determining a pedigree or degree of relationship for a heterozygous or homozygous subject.

Once a subject in need of treatment is identified as disclosed herein, the subject may be treated by administering an S100A13 or S100A3 protein, protein fragment, or analog in an amount that compensates for a loss of function of the mutant S100A13 and/or mutant S100A3 proteins. A functional analog of an S100A13 or S100A3 protein may have at least 70, 75, 80, 85, 90, 95, 96, 97, 98, 99, <100% sequence identity to SEQ ID NO: 1 or SEQ ID NO: 13. Preferably, a functional fragment or analog retains a function or a higher level of function that compensates for loss of function by a mutant form of S100A13 or S100A3.

In another embodiment, the treating comprises administering a nucleic acid encoding a functional S100A13 protein and/or encoding a functional S100A3 protein into the respiratory system or respiratory system cells of the subject, into the circulatory system or cells of the circulatory system, into muscle or other tissue of the subject, or in situ to a site of fibrosis. Cells of the circulatory system include red blood cells, platelets, leukocytes or white blood cells including lymphocytes, monocytes, granulocytes (e.g., neutrophyles, eosinophils, and basophils). Respiratory system cells include those that make up lung tissues such as bronchioles, epithelial cells, smooth muscle cells and alveoli. Some examples of respiratory system cells include type 1 epithelial cells, type 2 epithelial cells, and alveolar macrophages. In some embodiments, such cells may be loaded or transformed to express wild-type S100A13 or S100A3 proteins or their functional fragments or analogs. Such cells may be loaded with drugs or other agents that ameliorate the defective or aberrant phenomena associated with the mutant S100A13 or S100A3 proteins disclosed herein.

Depending on the target site or site of fibrosis, a protein, such as a wild-type S100A3 and/or S100A13 protein, or functional fragments thereof, or antibodies to mutant or wild-type S100A3 or S100A13 proteins, may be administered by injection, inhalation, or by a transdermal, intravenous, intranasal, intracranial, and/or intrathecal route. Preferably, the wild-type S100A13 or S100A3 proteins or their functional fragments or analogs are administered into the site of fibrosis.

These proteins may be incorporated into a pharmaceutically acceptable composition for administration by a particular route. In some embodiments, they may be encapsulated or incorporated into liposomes or prepared in a form that slowly releases them.

In some embodiments, whole cells expressing wild-type S100A13 or S100A3, including a patient's own cells or donor cells that are at least partially histocompatible with the patient are genetically engineered to express a wild-type S100A3 or wild-type S100A13 gene. For example, a subject's cells may be transformed with DNA vectors encoding functional S100A13 or S100A3 proteins to restore a more normal level of wild-type S100A3 or S100A13 in the respiratory system or other site of fibrosis. Gene therapy methods are known and incorporated by reference to Zhang, et al., Mol Ther. 2012 July; 20(7): 1298-1304 or to Dunbar, et al., Science 12 Jan. 2018.

In other embodiments, once a subject who has a mutant S100A13 or S100A3 gene is selected as described herein, a drug or agent may be administered that restores aberrant intracellular calcium homeostasis to a more normal level characterized by that in a subjects expressing a wild-type S100A3 or S100A13 gene; that increases a patient's capacity to tolerate oxidative stress such as an antioxidant; that protects mitochondria; or that compensates for altered extracellular matrix ("ECM") protein expression. For example, to restore calcium homeostasis a wild-type S100A13 or S100A3 protein or its functional analog may be administered. Drugs that inhibit transport of calcium include calcium channel blockers such as Amlodipine (Norvasc), Diltiazem (Cardizem, Tiazac), Felodipine, Isradipine, Nicardipine, Nifedipine (Adalat CC, Afeditab CR, Procardia), Nisoldipine (Sular), and Verapamil (Calan, Verelan). Some of these, such as nifedipine have been described as inhibiting collagen production. Drugs that can increase extracellular calcium levels which may also increase intracellular uptake of calcium include lithium, thiazide diuretics such as hydrochlorothiazide and chlorthalidone, calcium supplements including calcium carbonate, and vitamin D supplements such as calcipotriol. Drugs that can cause low calcium levels include bisphosphonates such as ibandronate and alendronate or zoledronic acid, prolia, sensipar, phenytoin, or cisplatin. Hormones that regulate calcium levels include parathyroid hormone, vitamin D and calcitonin. Those skilled in the medical arts may selection one or more, or a combination of drugs or agents that modulate intracellular calcium to adjust aberrant calcium homeostasis in patients deficient in wild-type S100A3 or S100A13 or to modulate or normalize other mutant phenotypes to be more like those in cells expressing wild-type genes. Lead drugs and agents include natural, synthetic, and recombinant S100A3 and S100A13 proteins and fragments thereof. These may be formulated in or with an acceptable pharmaceutical carrier or excipient.

In some embodiments antibodies may be used to selectively bind to, neutralize or remove mutant forms of S100A13 or S100A3 and may be used in conjunction with replacement of the removed mutant forms of these proteins with wild-type S100A13 or S100A3 or their functional analogs. To protect against oxidative stress or from damaging mitochondria, antioxidants, such as tocopherol, ascorbate, beta-carotene, vitamin A, lutein, lycopene, or selenium may be administered or drugs or supplements that protect mitochondria or promote their replication may be administered. These include alpha lipoic acid, L-carnitine, acetyl-carnitine, carnosine, CoQ10, PQQ (pyrroloquinoline quinone), NADH, phospholipids, or D-ribose. Other drugs useful for targeting and treating mitochondria include those described by Armstrong, J S, Br. J. Pharm. 2007 August, 151(8):1154-1165, and are incorporated by reference to this publication. To compensate for aberrant expression of MMPs, antibodies that bind to or neutralize excess MMPs found in patients expressing mutant S100A3 or S100A13 genes, such as MMP9, TIMP1, and MMP2 may be administered. Antibodies or other agents that normalize expression of the other proteins described herein, such as those described by FIGS. 6G-6H may be administered.

In the methods disclosed herein a subject may be at risk of, or manifest with, various types of fibrosis, such as organ fibrosis or pulmonary fibrosis. Other types of fibroses include pulmonary fibrosis such as cystic fibrosis, idiopathic pulmonary fibrosis, radiation-induced lung injury (for example, following cancer treatment); liver fibrosis, such as bridging fibrosis or cirrhosis; atrial fibrosis including endomyocardial fibrosis and that associated with myocardial infarction; glial scar and other types of fibrosis of the brain; arterial stiffness, arthrofibrosis, for example of the knee, shoulder, other joints; Crohn's disease, Dupuytren's contracture of the hands or fingers, keloid, mediastinal fibrosis, myelofibrosis, Peyronie's disease, nephrogenic systemic fibrosis, progressive massive fibrosis of the lungs (e.g., in coal workers), pneumoconiosis, retroperitoneal fibrosis, scleroderma, systemic sclerosis, or adhesive capsulitis.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 1A-1C. Clinical characteristics of three affected patients with pulmonary fibrosis ("PF") Show CT scans at initial presentation of the three patients showing central traction bronchiectasis (arrow). The distribution of fibrotic changes was peri-bronchovascular. The periphery of the lungs was spared. Global volume loss was seen retracting sub-pleural fat in the lateral portions of the fissures (arrow heads).

FIGS. 1D-1F. Clinical characteristics of three affected patients with pulmonary fibrosis. CT scans late in the disease course of patient 1. FIG. 1D: (i) Upper chest axial view. FIG. 1E: (ii) Lower chest axial view and FIG. 1F: (iii) coronal view. There was progression of the peribronchovascular fibrotic changes and volume loss. Patches of ground glass densities were randomly distributed.

FIG. 1G. Pulmonary function test results of patients and family members heterozygous for both the p.I80Gfs*13 (S100A13) and p.R77C (S100A3) variants.

FIGS. 1H-1J. Pathology of one affected patient; FIG. 1H: (i) a uniform infiltrate of interstitial chronic inflammation and mild fibrosis mainly involving alveolar wall; FIG. 1I: (ii) mild-sub-pleural fibrosis; FIG. 1J: (iii) advanced fibrosis and microscopic honeycombing.

FIGS. 2A, 2B, and 2C. These figures respectively show the pedigrees of Family 1A, 1B and 2. Open symbols unaffected; filled black symbols PF affected; (+) wild type sequence of S100A13/wild type "C" allele of S100A3; (−) 3 bp deletion of S100A13 (c.238-241delATTG)/mutant "T" allele of S100A3 (c.299C>T).

FIGS. 2F-2H respectively show the sequence chromatograms indicating the wild-type, homozygous affected and heterozygous carrier forms of the deletion mutant c.238-241delATTG which encodes p.I80Gfs*13 in S100A13.

FIGS. 3A-3B. Immunofluorescence micrographs showing expression of a S100A3 protein levels in normal/control lung tissue.

FIGS. 3C-3D. Immunofluorescence micrographs showing reduced expression of S100A3 in patient lung tissue.

FIGS. 3E-3F. Immunofluorescence micrographs showing expression of a S100A13 protein levels in normal/control lung tissue.

FIGS. 3G-3H. Immunofluorescence micrographs showing reduced expression of S100A13 protein in patient lung tissue.

FIG. 3J. Relative protein expression of S100A13 in normal control and lung tissues from patients. Significantly reduced expression of S100A13 is seen in patient's lung tissues.

FIGS. 3K and 3L: comparison of normal (FIG. 3K) with patient fibroblast tissue by fluorescence for S100A3. Confocal fluorescence laser scanning micrographs of showing the reduced expression of S100A3 proteins in skin fibroblasts isolated from patients compared to control (FIGS. 3K and 3L) and the corresponding western blots (FIG. 3M). Scale bar is 20 μm. Data are representative of three independent experiments.

FIG. 3M. Western blot of S100A3 protein in control, but not in patient tissue as compared to expression of control gene (beta-actin).

FIGS. 3N and 3O respectively compare fluorescence of control and patient tissue for S100A13. Confocal fluorescence laser scanning micrographs of showing the reduced expression of S100A13 proteins in skin fibroblasts isolated from patients compared to control and the corresponding western blots (FIG. 3P). Scale bar is 20 μm. Data are representative of three independent experiments.

FIG. 3P. Western blot S100A13 expressed in normal, but not in patient tissue, as compared to expression of control gene (beta-actin).

FIG. 4A. Intracellular calcium changes following stimulation of cultured skin fibroblasts isolated from a healthy control (blue) or a patient (red). Cells were stimulated with bradykinin (50 µM) (arrow).

FIG. 4B. The histograms show maximum response to bradykinin. Experiments were performed in live single cells using confocal laser scanning microscopy. Data are expressed as mean±SEM (n=23 and 24 for control and patients cells). Data are expressed as normalized fluorescence intensity ratio relative to the averaged three images obtained prior to the addition of stimulus and are representative of three independent experiments.

FIGS. 4C and 4D compare receptor mediated calcium change after stimulation with 10 ng/ml fibroblast growth factor 2 ("FGF-2"). Data are expressed as mean±SEM (n=10 and 7 cells for control (blue) and patient (red). Data are representative of 116 cells and 102 cells used in 8 and 12 independent experiments from patients and control fibroblasts, respectively. The histogram depicts the maximum changes evoked by FGF-2.

FIG. 4E. Relative maximum calcium response to ionomycin (2 µM) in skin fibroblasts from control and patients Data are expressed as mean±SEM n=28, 17, for control, patient, cells, respectively.

FIG. 4F. Mitochondrial calcium changes following stimulation of skin fibroblasts isolated from a healthy control (blue) or a patient (red), with bradykinin (50 µM). Experiments were performed in live single cells using confocal laser scanning microscopy as above.

FIGS. 5E-5F. Flow cytometry of skin fibroblasts isolated from patient and control cells stained with Mitotracker Green. FIG. 5F shows mean fluorescence intensity in patients and control cells. Data were performed in triplicate and are representative of at least three independent experiments using $10^6$ cells/sample.

FIGS. 5G-5H. Transmission electron microscopy (TEM) scans of cells isolated from healthy control and patient's cells depicting differences in mitochondrial size (arrows) and loss of cristae. TEM showed evidence of mitochondrial damage, reduced cristae and reduced rough endoplasmic reticulum (RER) in patient samples (FIG. 5G) compared to control (FIG. 5H).

FIG. 6A-6B. Western blots of MMP9 expression by skin fibroblasts isolated from healthy controls and patient.

FIG. 6C-6D. Western blots of TIMP1 expression by skin fibroblasts isolated from healthy controls and patient.

FIG. 6E-6F. Western blots of MMP2 expression by skin fibroblasts isolated from healthy controls and patient.

FIG. 6G. Differential expression of matrixins (MMP1, 3 and 14).

In FIGS. 6G and 6H normalized protein abundance of significantly differentially expressed proteins between patient and control samples are shown (a fold change >1.5, and at FDR-3%). Yeast alcohol dehydrogenase standard (P00330) at a concentration of 200 fmol per injection was used for absolute quantifications of all identified proteins. The histogram bars corresponds to the average protein expressions between the two sample groups using label-free LC/MS expression analysis platform on the Progenesis QIfp (Nonlinear Dynamics/Waters). Data are expressed as mean±SEM (n=3). P values are indicated on top of the black horizontal bars.

FIG. 7A-7F. High resolution CT scans of two subjects showing central traction bronchiectasis (arrow). The distribution of fibrotic changes is peri-bronchovascular and central. The periphery of the lungs is spared. Global volume loss is seen evident by retracting sub-plural fat in the lateral portions of the fissures (arrow heads).

FIG. 7G. Pulmonary function test of patients.

FIG. 7H shows pathology of one affected patient. Interstitial inflammation and fibrosis are uniform by lower power with no temporal heterogeneity.

FIG. 7I: Shows focal advanced interstitial fibrosis with early microscopic honeycombing.

DETAILED DESCRIPTION OF THE INVENTION

Figure 2A:
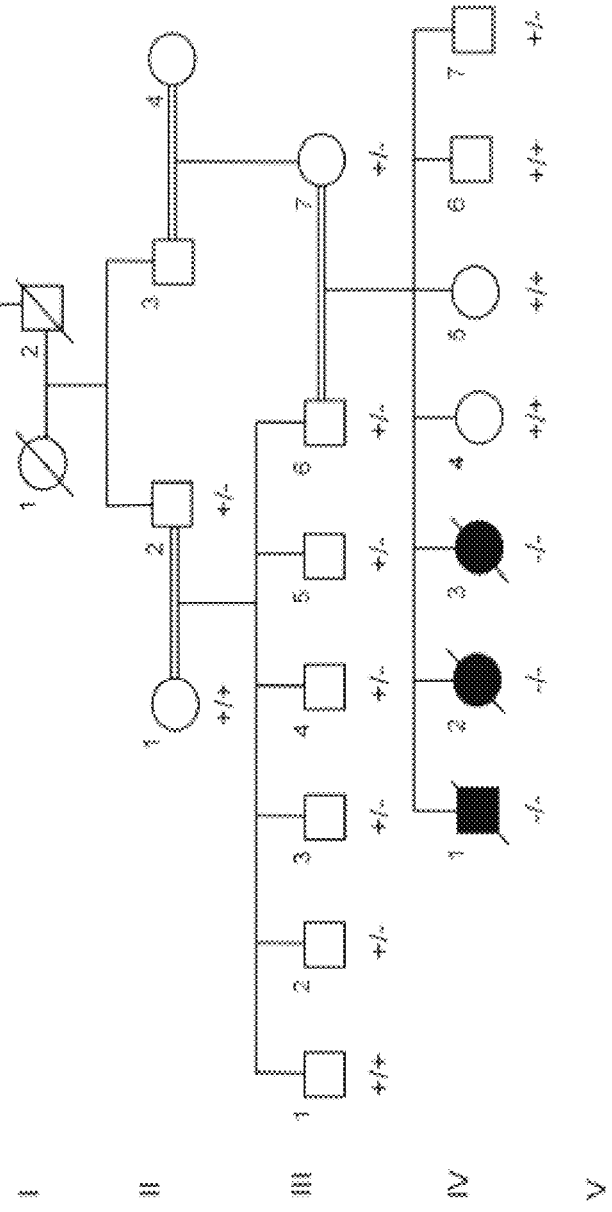

Embodiments of the present disclosure will now be described more fully hereinafter with reference to the accompanying drawings, in which some, but not all embodiments of the disclosure are shown.

S100 Family.

S100A3 and S100A13 protein are members of a large family of acidic, low molecular weight calcium binding proteins characterized by two $Ca^{2+}$-binding motifs (EF-hand). More than 20 different members have been identified with diverse functions in cell growth and differentiation, cancer, skin barrier functions, signal transduction and sterile inflammation. The proteins are found exclusively in vertebrates; and members exist as homodimers, heterodimers and multi-oligomers, displaying cell- and tissue-specific pattern of expression with significant structural similarities to calmodulins. Although the proteins function intracellularly to control calcium homeostasis, secreted members exhibit cytokine-like effects through binding to a number of receptors including the receptor for advanced glycation end products (RAGE). Higher order molecular structures are quite common among S100 proteins and are biologically relevant as demonstrated by the higher affinity of S100B tetramer for RAGE than its dimer. Of all the S100 family, S100A3 has the highest content of cysteine and the highest affinity for $Zn^{2+}$. It is expressed in human hair cuticle where it is citrulinated and tetramerized to improve its $Ca^{2+}$-binding ability and endocuticle rigidity of aged hair. Human S100A3 was shown to spontaneously homo-tetramerize in hair cuticle cells and in mice, S100A3 blockade inhibits hair growth and evokes marked reduction in tumor growth and invasiveness. S100A13 on the other hand is associated with non-classical pathway of IL-1alpha and FGF-1 secretion (Landriscina et al 2001 JBC 276, 25549-25557, and Mohan and Yu 2011 JBC, 286, 14608-14617—incorporated herein by reference). It was demonstrated to form a heterotetrameric complex with IL-1alpha and its association with HMGA1 modulates thyroid cancer proliferation and invasion (Zhong et al, 2016, J Translational Medicine, 14:80—incorporated herein by reference). S100A13 was also reported to interact with synaptotagmin, a protein that is intimately involved in neurotransmitter release.

A mutation is known in the S100A3 gene that introduces an eleventh cysteine residue which replaces arginine residue at position 77. The p.R77C mutation is classified as an SNP and has been found in the homozygous state in the ExAC database (hypertext transfer protocol:///exac.broadinstitute.org/variant/1-153520235-G-A—incorporated herein by reference).

A frameshift mutation in S100A13 can result in a truncated form of the protein. Sequencing of the full intronic regions and 3' untranslated region of S100A3 and S100A13 excluded any other disease-associated variations in the S100A3 and S100A13 genes' sequence in the affected members of both families. The mutation did not alter any predicted microRNA binding sites that could affect protein expression.

A S100A13 polynucleotide typically encodes a S100 calcium-binding protein S100A13 protein or fragments or variants of an S100A13 protein. The S100A13 polynucleotide (SEQ ID NO: 13) encodes a wild-type functional S100A13 polypeptide (SEQ ID NO: 14). One type of mutant S100A13 polypeptide, which lacks the full functionality of wild-type S100A13, comprises the frameshift mutation c.238-241delATTG. The polynucleotide of SEQ ID NO: 15 is one example of such a mutant S100A13 polynucleotide. Polynucleotides comprising SEQ ID NOS: 13 and 15, respectively encode the S100A13 polypeptides of SEQ ID NOS: 14 and 16. In some embodiments, a polynucleotide will encode a fragment of the S100A13 protein that retains at least one epitope or functional segment of a full-length S100A13 protein. Variant S100A3 polynucleotides can have sequences that are at least 70, 80, 90, 95, 96, 97, 98, 99 or <100% identical to those of SEQ ID NOS: 13 or 15. A polymorph or variant may have 1, 2, 3, 4, 5, 6, 7, 8, 9, 10 or more nucleotide deletions, substitutions or insertions compared to a naturally occurring S100A13 polynucleotide. This term includes alternatively spliced variants of S100A13 RNA. Primer pairs which may be used to amplify S100A13 polynucleotides, for example, as present in or derived from a control or patient sample, include forward primer 5'-CATCTGCTCAAGGATGTGGG (SEQ ID NO: 19) and reverse primer 5'-TCCTGATCTTCAGGTCTTT (SEQ ID NO: 20).

A S100A3 polynucleotide typically encodes calcium-binding protein S100A3 protein or fragments or variants of an S100A3 protein. The S100A3 polynucleotide (SEQ ID NO: 1) encodes a wild-type functional S100A13 polypeptide (SEQ ID NO: 2). One type of mutant S100A3 polypeptide, which lacks the full functionality of wild-type S100A3, comprises the 229C>T mutation. The polynucleotide of SEQ ID NO: 3 is one example of such a mutant S100A3 polynucleotide. Polynucleotides comprising SEQ ID NOS: 1 and 3, respectively encode the S100A3 polypeptides of SEQ ID NOS: 2 and 4. In some embodiments, a polynucleotide will encode a fragment of the S100A3 protein that retains at least one epitope or functional segment of a full-length S100A3 protein. Variant S100A3 polynucleotides can have sequences that are at least 70, 80, 90, 95, 96, 97, 98, 99 or <100% identical to those of SEQ ID NOS: 1 or 3. A polymorph or variant may have 1, 2, 3, 4, 5, 6, 7, 8, 9, 10 or more nucleotide deletions, substitutions or insertions compared to a naturally occurring S100A3 polynucleotide. This term includes alternatively spliced variants of S100A3 RNA.

BLASTN may be used to identify a polynucleotide sequence having at least 70, 75, 80, 85, 90, 95, 96, 97, 98, 99, <100, or and 100% (or any intermediate %) sequence identity to a reference polynucleotide such as a polynucleotide encoding a S100A13 or S100A3 protein. A representative BLASTN setting optimized to find highly similar sequences uses an Expect Threshold of 10 and a Wordsize of 28, max matches in query range of 0, match/mismatch scores of 1/-2, and linear gap cost. Low complexity regions may be filtered/masked. Default settings are described by and incorporated by reference to hypertext transfer protocol://blast.ncbi.nlm.nih.gov/Blast.cgi?PROGRAM=blastn&BLAST_PROGRAMS=megaBlast&PAGE_TYPE=BlastSearch&SHOW_DEFAULTS=on&LINK_LOC=blasthome (last accessed Sep. 10, 2018).

Primer-BLAST may be used to find primers for amplifying the polynucleotides disclosed herein including those encoding S100A13 wild-type (SEQ ID NO: 13), S100A13 frameshift mutant (SEQ ID NO: 15), S100A3 wild-type (SEQ ID NO: 1) and S100A3 229C>T (SEQ ID NO: 3) as well as other S100A family polynucleotides; see hypertext transfer protocol//_www.ncbi.nlm.nih.gov/tools/primer-blast/index.cgi?ORGANISM=9606&INPUT_SEQUENCE=NM_001024210.2&LINK_LOC=nuccore (last accessed Jun. 25, 2019, incorporated herein by reference).

The term S100A13 polypeptide describes a class of polypeptides that have about 70, 75, 80, 85, 90, 95, 96, 97, 98, 99, <100 or 100% sequence identity or similarity to SEQ ID NO: 14. This class includes a wild-type, functional S100A13 polypeptide of SEQ ID NO: 14 and other functional natural variants as well as a non-functional mutant S100A13 polypeptide of SEQ ID NO: 16. S100A13 typically comprises 2 EF-hand calcium binding motifs which may be disrupted or modified in mutant forms of S100A3.

A mutant S100A13 protein will have a non-wild-type amino acid sequence, and will typically exhibit aberrant expression, folding, and/or activity compared to wild-type S100A13 protein of SEQ ID NO: 14. One example of such a mutant S100A13 protein is described by SEQ ID NO: 16 which contains frameshift mutation p.I80Gfs*13. The term S100A13 polypeptide also includes functional fragments of S100A13 which exert at least one biological, physiological or immunological activity or function of a wild-type S100A13 polypeptide. A fragment may contain up to 5, 10, 15, 20, 30, 40, 50, 60, 70, 80, 90, 95, 96, 97, 98, 99 or <100% of the residues of a native or variant S100A13 polypeptide. A fragment may contain a segment comprising a linear epitope or a segment that binds to a receptor recognized by the full-length S100A13 protein.

The term S100A3 polypeptide describes a class of polypeptides that have about 70, 75, 80, 85, 90, 95, 96, 97, 98, 99, <100 or 100% sequence identity or similarity to SEQ ID NO: 2. This class includes a wild-type, functional S100A3 polypeptide of SEQ ID NO: 2 and other functional natural variants as well as a non-functional mutant S100A3 polypeptide of SEQ ID NO: 4. S100A3 typically comprises 2 EF-hand calcium binding motifs which may be disrupted or modified in mutant forms of S100A3.

A mutant S100A3 protein will have at least a partially non-wild-type amino acid sequence, and will typically exhibit aberrant expression, folding, and/or activity compared to wild-type S100A3 protein of SEQ ID NO: 2. One example of such a mutant S100A3 protein is described by SEQ ID NO: 4 which contains the R77C substitutional mutation.

The term S100A3 polypeptide includes functional fragments of S100A3 which exert at least one biological, physiological or immunological activity or function of a wild-type S100A3 polypeptide. A fragment may contain up to 5, 10, 15, 20, 30, 40, 50, 60, 70, 80, 90, 95, 96, 97, 98, 99 or <100% of the residues of a native or variant S100A3 polypeptide. A fragment may contain a segment comprising a linear epitope or a segment that binds to a receptor recognized by the full-length S100A3 protein.

A non-functional or partially functional S100A13 protein, S100A3 protein, or S100A family protein may exhibit no, or lower, activity or a different or defective activity with respect to one or more intracellular and extracellular functions of the corresponding wild-type S100 protein including regulation of protein phosphorylation, activity as a transcription factor, regulation of $Ca^{2+}$ homeostasis, role in the dynamics of cytoskeleton constituents, enzyme activities, cell growth and differentiation, or in inflammatory responses.

A mutant S100A13 or S100A3 polypeptide may be expressed at, or otherwise present at, a lower or higher level than a wild-type S100A13 polypeptide inside of a cell in the cytoplasm or nucleus or inside of mitochondria, for example, a mutant protein may be expressed at a let of at least 10, 20, 30, 40, 50, 60, 70, 80, 90, 100, 110, 120, 130, 140, 150, 160, 170, 180, 190 or 200% of that of the corresponding wild-type protein.

BLASTP can be used to identify an amino acid sequence having at least 70%, 75%, 80%, 85%, 87.5%, 90%, 92.5%, 95%, 96, 97.5%, 98%, 99%, <100% or 100% (or any intermediate %) sequence identity or similarity to a reference amino acid such as a S100A3 or S100A13 protein using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to hypertext transfer protocol://blast.ncbi.nlm.nih.gov/Blast.cgi?PROGRAM=blastp&PAGE_TYPE=BlastSearch&LINK_LOC=blasthome (last accessed Jun. 25, 2019).

A S100A3 or S100A13 polypeptide, variant or fragment thereof may be produced by methods known in the art including by cloning and recombinant expression in a host cell or by chemical synthesis. Many protein expression and purification systems are known and incorporated by reference to hypertext transfer protocol secure://_en.wikipedia.org/wiki/Protein_production (last accessed Jul. 1, 2019).

Single Nucleotide Polymorphisms and Other Polymorphisms.

A polymorphism in an S100A13 or S100A3 polynucleotide may be detected or analyzed by methods known in the art, including by methods using the polymerase chain reaction, DNA sequencing, capillary electrophoresis, mass spectrometry; single-strand conformation polymorphism (SSCP); single-base extension; electrochemical analysis; denaturating HPLC and gel electrophoresis; restriction fragment length polymorphism; or hybridization analysis. Typically, the polymorphism will occur in a coding region for the S100A13 or S100A3 protein, such as a missense mutation causing an amino acid residue substitution, but a polymorphism may also occur outside of the coding region, for example, in a flanking DNA sequence.

Homozygous affected subjects typically have two copies of a non-functional or aberrant mutant S100A13 or S100A3 gene.

Heterozygous Carriers.

Some individuals have one wild-type S100A3 and/or one wild-type S100A13 gene and one mutant S100A3 and/or S100A13 gene and thus are heterozygous for this gene(s). Carrying a single copy of the nonfunctional mutant gene for S100A13 or S100A1 may cause altered responses to certain physiological stimuli and negatively impact lung function, especially lower lung functions including compromising lung reserve. A subject carrying one copy of a mutant S100A13 or S100A3 gene may exhibit a milder aberrant phenotype than a subject carrying two copies. Moreover, a subject who is heterologous for a mutant S100A13 or S100A3 gene is a genetic carrier of this gene and can produce children who are homozygous or heterozygous for the S100A13 of S100A3 mutation depending on the genetic background of the other parent.

Treatments for fibrosis associated with mutant S100A13 or S100A3 genes include administering functional S100A13 or S100A3 protein to a subject deficient in or totally lacking functional S100A3 or S100A13 protein. As disclosed or shown herein the effects of a mutation in S100A13 or S100A3 on cellular responses can be reversed by administration of functional, wild-type S100A3 or S100A13 protein.

Functional S1001A13 and/or S100A3 protein may be administered systemically and/or locally, preferably directly or indirectly into the respiratory system or other site of fibrosis. For pulmonary fibrosis, functional S100A13 or S100A3 protein may be administered into the lungs using a nebulizer or metered dose inhaler to rectify abnormal cellular responses or halt the progression of lung fibrosis. Functional S100A13 or S100A3 protein and other active ingredients, such as antibodies that selectively bind to non-functional S100A13 and/or S100A3 protein, are preferably prepared in a form that can reach and persist in target respiratory tissues such as the lungs, bronchi and other airways.

A pulmonary route of administration offers many advantages including noninvasive delivery of protein and peptide-based drugs, absorption of a drug through the lungs by simple diffusion and carrier-mediated transport, often permitting a decrease in the amount of drug to be administered effectively, fast adsorption and better patient compliance that other parenteral routes. However, functional S100A13 or S100A3 protein, or other active ingredients like antibodies that bind to and remove or neutralize non-functional, mutant S100A13 or rS100A3 protein, may be administered by other routes including in situ to a fibrotic site, intravenously, intraperitoneally, subcutaneously, intramuscularly, and topically.

Oral administration may be contemplated so long as the functional S100A13 or S100A3 protein is administered in a form that is not digested prior to reaching a target site or being adsorbed and eliminated by the body.

A nebulizer is a drug delivery device that administered a drug, such as functional S100A13 or functional S100A3 protein or antibodies that bind to non-functional or other medicaments in an inhalable form. Nebulizers for treatment of cystic fibrosis, asthma, COPD and other respiratory diseases are known and incorporated by reference to hypertext transfer protocol secure://_en.wikipedia.org/wiki/Nebulizer (last accessed Jul. 2, 2019, incorporated by reference). These include soft mist inhalers, jet nebulizers, ultrasonic wave nebulizers, and nebulizers using vibrating mesh technology.

A metered-dosage inhaler is another drug delivery device that delivers a selected or metered amount of a medication, such as functional S100A13 or S100A3 protein or an antibody that binds to non-functional or mutant S100A13 or S100A3 protein. Typically, this device produces and releases an aerosol of micrometer-sized particles that are inhaled. In some cases, the particles may be a dry powder in others as a mist or in a semiliquid form. Metered-dose inhalers and their various components, propellants, excipients and other elements are described by and incorporated by reference to hypertext transfer protocol secure://_en.wikipedia.org/wiki/Metered-dose_inhaler (last accessed Jul. 2, 2019, incorporated by reference). An inhalable composition may be formulated in the form of a hydrofluoroalkane inhaler or HFA (metered dose inhaler or MDI), dry powder inhaler (DPI), or as a nebulizer solution.

Functional S100A13 protein, S100A3 protein, or antibodies that bind to non-functional S100A13 or S100A3 protein or other medicaments may be administered as a bolus, or over a period of time, such as at 0.25, 0.5, 1, 2, 3, 4, 5 or more hour intervals. Dosages of functional S100A13 or functional S100A3 protein may range from 1, 2, 5, 10, 20, 50, 100, 200, 500 or more picomoles to 1, 2, 5, 10, 20, 50, 100, 200, 500 or more millimoles.

Modes of administration for functional S100A13, functional S100A3, or other active ingredients of the invention include by nebulizer, oral, sublingual, rectal, topical, parenteral (other than IV and IM), intravenous injection, intramuscular injection and intraperitoneally. Drugs, functional S100A3 or S100A13 or the other agents described herein may be injected into or around a fibrotic site.

Injection of DNA encoding a functional S100A13 protein or functional S100A3 protein may also be used as well as gene therapy of cells, such as by transformation of pulmonary cells or cells at least partially residing in the lungs with a nucleic acid encoding functional S100A13 or functional S100A3 protein.

Intravenous administration delivers a drug, such as functional S100A13 or S100A3 protein or an antibody that binds to non-functional S100A13 protein or non-functional S100A3 protein directly into a vein. It is usually considered one of the fastest ways to deliver a drug. A drug or agent may be administered as a bolus, for example, by i.v. push or by injection with a syringe, or by continuous infusion over a period of 0.0.25, 0.5, 1, 2, 3, 4, 5 or more hours.

Antibody-based treatments include administration of antibodies that selectively bind to non-functional S100A13 protein and/or non-functional S100A3 protein and inactivate, promote its removal, or remove it so that subsequently administered wild-type or functional S100A13 or S100A3 protein may exert a therapeutic function by replacing non-functional S100A13 protein. Antibodies that selectively bind to mutant S100A13 or S100A3 protein, but have a lower or no binding affinity for wild-type or functional S100A13 or S100A3 protein may be administered systemically or locally, including into the respiratory system. These may be administered before, at the same time as, or after administration of a functional S100A13 or S100A3 protein. In some embodiments, an antibody that binds to non-functional mutant S100A13 or S100A3 protein may be pre-administered and after a time sufficient for removal or reduction of non-functional S100A13 or S100A3 protein levels by followed by administration of a functional S100A13 or S1003 protein. In some embodiments, other functional S100 family proteins may be administered in combination with functional S100A13 or S100A3 protein, or antibodies that bind to other non-functional S100 family proteins may be administered in combination with an antibody that binds to non-functional S100A13 or S100A3 protein.

An antibody may be polyclonal, monospecific, or monoclonal, preferably monoclonal for purposes of uniformity and standardization. Antibodies include IgA, IgE, IgG and IgM as well as their various subclasses. Secretory antibodies, such as sIgA or pentameric IgM may be used. Antibody fragments or antibody conjugates that retain an ability to recognize and bind to non-functional S100A13 or S100A3 protein may also be used. Antibodies according to the invention can be made by any method known in the art. For example, the general methodology for making monoclonal antibodies using hybridoma technology is well known (Kohler, G. and Milstein, C., 1975; Kozbar et al. 1983). In one embodiment, the alternative EBV immortalization method described in WO2004/076677 is used. Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Compositions. A functional S100A13 and/or S100A3 protein or other active ingredient of the invention may be formulated as a pharmaceutically acceptable composition, for example, with a physiologically acceptable carrier for pulmonary or intravenous administration. As used herein, a "composition" refers to a mixture of the active ingredient with at least one other chemical component, such as a pharmaceutically acceptable carrier or excipient. One purpose of a composition is to facilitate administration of a functional S100A13 and/or S100A3 protein or other active ingredients of the invention to a subject.

Depending on the intended mode of administration, the composition can be in the form of solid, semi-solid, liquid, or aerosol dosage forms, such as solutions, powders, tablets, suppositories, pills, capsules, powders, liquids, or suspensions, preferably in unit dosage form suitable for single administration of a precise dosage.

The phrase "pharmaceutically acceptable" as used herein refers to compounds, counter ions, materials, compositions, and/or dosage forms which are, within the scope of sound medical judgment, suitable for use in contact with the tissues of human beings without excessive toxicity, irritation, allergic response, or other problem or complication and commensurate with a reasonable benefit/risk ratio. A composition is typically a combination of an active ingredient with a carrier or excipient, inert or active, making the composition especially suitable for diagnostic or therapeutic use in vivo, ex vivo, or in vitro.

The term active ingredient, as used herein, refers to an ingredient in the composition that is biologically active, for example a functional S100A3 and/or S100A13 protein, antibody that binds to non-functional or mutant S100A13 or S100A3 protein or polynucleotide encoding these proteins. Other active ingredients include, but are not limited to, those that exert a substantial pharmacokinetic or pharmacodynamic activity when in admixture with the active ingredients of the invention, for example, other excipients, buffers, or stabilizers, or other drugs approved for administration to the respiratory system.

As used herein, a pharmaceutically acceptable carrier refers to a carrier or diluent that does not cause significant irritation to an organism, does not abrogate the biological activity and properties of the administered active ingredient, and/or does not interact in a deleterious manner with the other components of the composition in which it is contained.

The term carrier encompasses any excipient, binder, diluent, filler, salt, buffer, solubilizer, lipid, stabilizer, or other material well known in the art for use in pharmaceutical formulations, for example, for intravenous administration a carrier may be sodium chloride 0.9% or mixtures of normal saline with glucose or mannose. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid or tocopherol; low molecular weight polypeptides having 2, 3, 4, 5, 6, 7, 8, 9, 10 or fewer residues; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI. Inc.; Bridgewater, N.J.), polyethylene glycol (PEG), and PLURONICS® (BASF; Florham Park, N.J.).

In some embodiments an active ingredient of the invention, such as functional S100A13 and/or S100A3 protein (or cells expressing them) may be administered in a carrier used to administer other drugs to the respiratory system, such as carriers for anti-inflammatory drugs. It may also be administered in combination with an anti-inflammatory drug such as an inhaled steroid such as Beclomethasone dipropionate (Qvar), Budesonide (Pulmicort), Budesonide/Formoterol (Symbicort)—a combination drug that includes a steroid and a long-acting bronchodilator drug, Fluticasone (Flovent), Fluticasone inhaled powder (Arnuity Ellipta), Fluticasone/Salmeterol (Advair)—a combination drug that includes a steroid and a long-acting bronchodilator drug, Mometasone (Asmanex), or Mometasone/formoterol (Dulera)—a combination drug that also includes a long-acting bronchodilator drug. In some embodiments one or more NSAIDs may be administered as additional active ingredients, these include aspirin, celecoxib (Celebrex), diclofenac (Cambia, Cataflam, Voltaren-XR, Zipsor, Zorvolex), diflunisal (Dolobid), etodolac, ibuprofen (Motrin, Advil), indomethacin (Indocin), ketoprofen, ketorolac (Toradol), nabumetone, naproxen (Aleve, Anaprox, Naprelan, Naprosyn, oxaprozin (Daypro), piroxicam (Feldene), salsalate (Disalsate), sulindac) or tolmetin. A secondary active ingredient may be administered by the same or by a different route or mode of administration.

For therapeutic purposes, formulations for parenteral administration can be in the form of aqueous or non-aqueous isotonic sterile injection solutions or suspensions. The term parenteral, as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration, preferably in a digestion-resistant form such as an enteric coating. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and nonionic detergents, polyethylene glycols can be used. Mixtures of solvents and wetting ingredients such as those discussed above are also useful.

DNA- or RNA-based pharmaceuticals In some embodiments, DNA encoding an S100A13 protein or a S100A3 protein of the invention may be replicated or synthesized by known methods. The DNA is then formulated for administration to a subject, for example, by pulmonary, intravenous, subcutaneous, intramuscular, intrapulmonary, or intralymphatic administration. Gene therapy methods are known and incorporated by reference to Zhang, et al., Mol Ther. 2012 July; 20(7): 1298-1304 or to Dunbar, et al., Science 12 Jan. 2018

In some embodiments, polynucleotides that encode functional S100 family proteins other that S100A13 may be administered in combination with a polynucleotide that encodes a functional S100A13 or S100A3 protein. Members of the S100 family include those encoded by S100A1, S100A2, S100A3, S100A4, S100A5, S100A6, S100A7 (psoriasin), S100A8 (calgranulin A), S100A9 (calgranulin B), S100A10, S100A11, S100A12 (calgranulin C), S100A13, S100A14, S100A15 (koebnerisin), and S100A16 genes or coding polynucleotides.

In some embodiments, mRNA encoding a S100A13 and/or S100A3 polypeptide or other S100 family polypeptide of the invention may be produced by transcribing or otherwise producing an RNA molecule corresponding to DNA encoding the polypeptide by known methods. The RNA is then formulated for administration to a subject, for example, by in situ to site of fibrosis, intravenous, subcutaneous, intramuscular, intrapulmonary, or intralymphatic administration.

Other Active Ingredients.

In some embodiments, other active ingredients in addition to a functional S100A3 and/or S100A13 protein or polynucleotide encoding it, or to an antibody or antibody fragment that binds to non-functional S100A3 and/or S100A13 proteins may be incorporated into a composition or separately administered in conjunction with at least one active ingredient of the invention. These include anti-inflammatory agents, colchicine, corticosteroids, including inhalable corticosteroids like flunisolide,' fluticasone furoate,' fluticasone propionate,' triamcinolone acetonide,' beclomethasone dipropionate, and Budesonide; immunosuppressants such as cyclophosphamide, azathioprine, methotrexate, penicillamine, and cyclosporine, or cytokines, such as IFN-gamma.

Protease inhibitors may be administered to increase the biological life of functional S100A13 and/or S100A3 protein or other active ingredients of the invention or otherwise inhibit protease activity during treatment; see hypertext transfer protocol secure://_www.ddw-online.com/therapeutics/p148402-protease-inhibitor-therapeutics-for-respiratory-disease-winter-03.html, last accessed Jun. 21, 2019, incorporated by reference).

In some embodiments, one or more chaperonins may be administered to correct protein misfolding, along with an active component of the invention such as along with a functional S100A13 or S100A3 protein. Chaperonins are incorporated by reference to Elena L. Rudashevskaya, Thomas Stockner, Michael Trauner, Michael Freissmuth and Peter Chiba. *Pharmacological correction of misfolding of ABC proteins*. Drug Discov Today Technol. 2014 June; 12(100): e87-e94. doi: 10.1016/j.ddtec.2014.03.009. PMCID: PMC4039138 PMID: 25027379. In another embodiment, the mutant S100A3 or S100A13 proteins described herein may be used as targets for screening of chaperonin compounds that increase or restore wild-type S100A13 functionality. Such a method would involve contacting a mutant S100A3 or S100A13 protein or a cell expressing it with a chaperonin, detecting an increase in at least one wild-type S100A3 or S100A13 activity, and, optionally, treating a subject who expresses a mutant S100A3 or S100A13 protein with a chaperonin that increases the wild-type activity.

Antioxidants, such as tocopherol, ascorbate, beta-carotene, vitamin A, lutein, lycopene, or selenium or other pharmaceutically acceptable antioxidants may be administered optionally in combination with oxygen before, during or after therapy with an active ingredient of the invention.

Improvement in status of pulmonary fibrosis may be determined by CT scanning to show a degree of general fibrosis or for staging according to CT results and lung function tests. Improvement is measured by halting the progress of the disease or by reducing the already existing fibrosis which can be determined using CT scans and lung functional tests.

Pulmonary fibrosis is one of the leading indications for lung transplantation. The disease can be progressive resulting in distortion of extracellular matrix (ECM), inflammation, fibrosis and eventual death. The inventors have identified patients born to consanguineous parents from three families (two of which are related) presenting with interstitial lung disease. Out of a combined 13 patients, 9 developed respiratory failure and subsequently died.

The combination of a unique pattern of early onset lung fibrosis, distinctive radiological findings, in addition to type 2 respiratory failure represents a novel clinical subtype of familial pulmonary fibrosis.

Molecular genetic investigation of all three families revealed a hypomorphic variant in S100A3 and a novel truncating mutation in S100A13, both occurring in an autosomal recessive pattern and segregating in the affected. Additional family members were either heterozygous carriers or wild-type normal for both variants.

Analysis of patient-derived fibroblasts demonstrated the significantly reduced levels of S100A3 and S100A13. Further analysis demonstrated aberrant intracellular calcium homeostasis, These data demonstrate that S100A3/S100A13 are involved in the regulation of collagen synthesis and suggest a calcium dependent therapeutic approach in the management of pulmonary fibrosis.

EXAMPLES

The following Examples illustrate various aspects of the present invention. They are not to be construed to limit the claims in any manner whatsoever.

Families and Brief Case Description.

Figure 8:
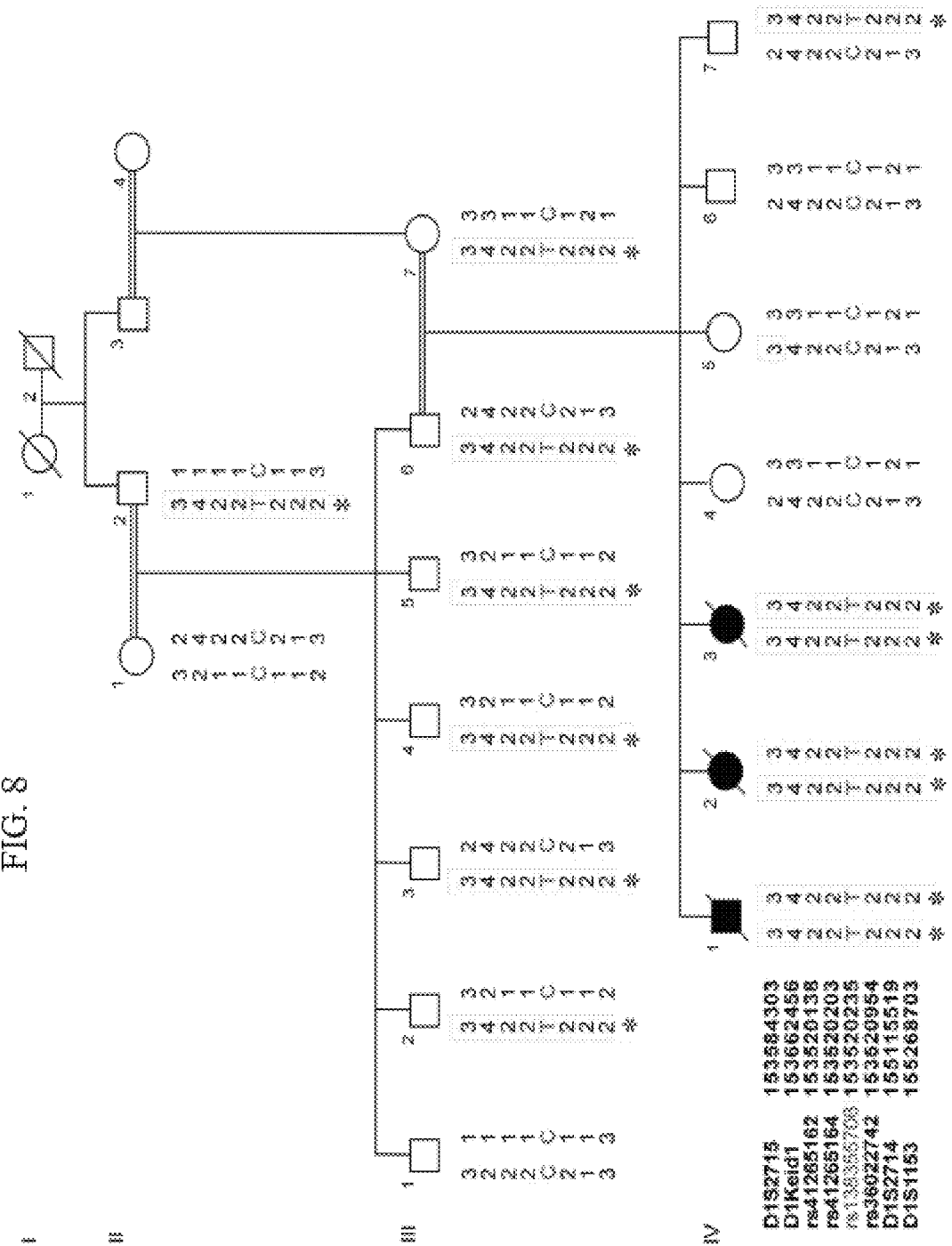
FIG. 8. The pedigree of Family 1A with haplotype and genotype analyses; disease haplotype is highlighted in yellow/gray. Genotype of variants in genes S100A3: c.229 C>T transition (rs138355706) causing p.R77C and S100A13: c.238-241delATTG causing p.I80Gfs*13 is denoted with "*".
Figure 9:
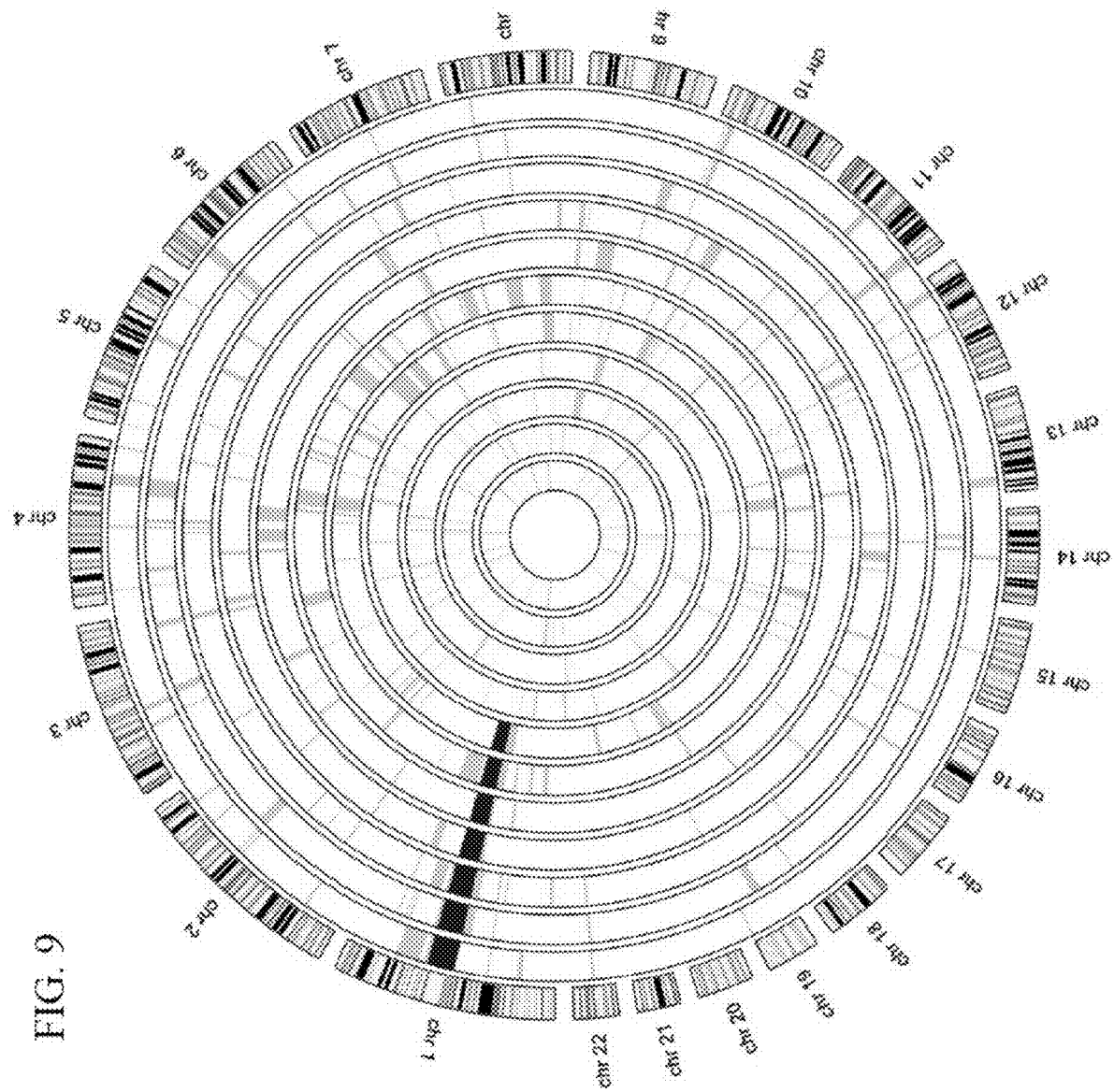
FIG. 9. Circular ideogram of the genome (Agile Multi-Ideogram; hypertext transfer protocol:/_/dna.leeds.ac.uk/) showing the exclusive region of homozygosity (ROH) between the affected individuals in the all families (black bands in outer rings 5-11) on Chromosome 1 (chr1:120,127,864-154,749,047 bp; UCSC genome browser, build hg19), that is not shared with any of the unaffected individuals (light gray—inner 4 rings). Gray bands in outer rings 5-11 denote ROHs present in affected members. Light gray bands in inner 4 rings depict ROHs present in unaffected members.

Family 1A. Three siblings (two girls and one boy) from a total of seven children were born healthy to consanguineous Saudi Arabian parents after normal pregnancies and deliveries. The parents did not report any medical problems until all three children developed respiratory fibrosis at a young age. All three affected siblings had an identical clinical presentation and course (FIGS. 1A-1F). All developed dyspnea in adolescence and aside from the lung abnormalities, complete and extensive medical examinations revealed normal appearance, development and laboratory findings. Fibrosis was revealed by chest CT imaging (FIGS. 1A-1F) and pulmonary function testing indicated severe restriction and impaired oxygen transfer (FIG. 1G). The subjects underwent extensive medical investigations in Saudi Arabia and the USA, resulting in exclusion of known causes of lung fibrosis (including genetic). Respiratory symptoms worsened with age, and all 3 patients developed chronic type 2 respiratory failure. Two of the siblings underwent lung transplantation at ages 22 years and 23 years of age, but died due to primary graft failure. The third sibling died from respiratory failure at 23 years of age. A lung autopsy from one of the subjects revealed non-specific fibrosis-like pattern with microscopic honeycombing (FIGS. 1H-1J). FIG. 2A and FIG. 8 describe Family 1A.

Figure 2B:
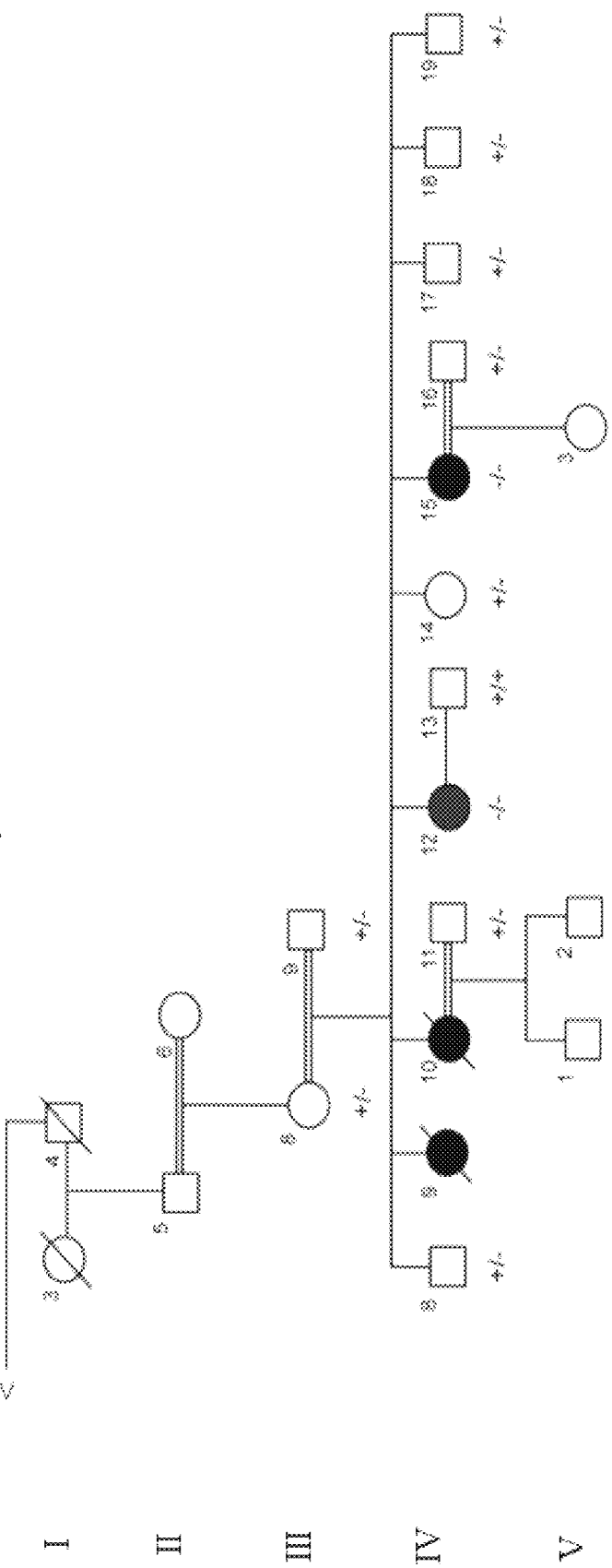
Figure 2D:
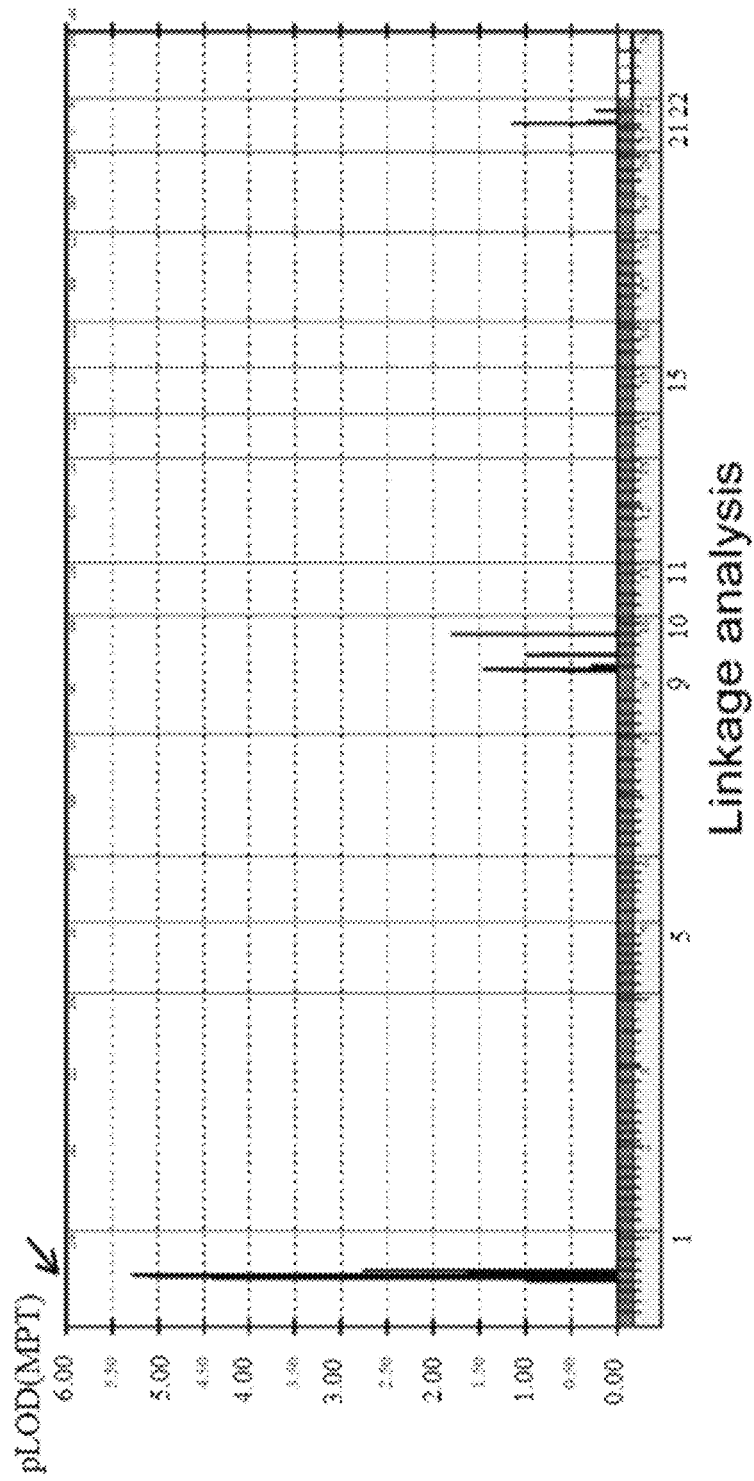
FIG. 2D shows linkage analysis resulting in a peak where the maximum multipoint LOD score was 5.28 corresponding to chromosome 1p12-q21.3.

Family 1B. Four affected girls from a total of nine children were born healthy to consanguineous Saudi Arabian parents after normal pregnancies and deliveries were enrolled at a later stage of the study. The mother of this family is the second cousin from both of the parents of Family 1A. Two of the girls died due to respiratory failure before the family presented at the pulmonary clinic and the other two patients were subjected to full clinical and molecular investigations. Similar to the previous family, extensive workup revealed no known causes of pulmonary fibrosis. CT imaging revealed identical findings of fibrosis and pulmonary function tests showed severe restriction. FIG. 2B describes Family 1B.

Family 2: A second family presenting with a very similar clinical pattern to Family 1 was identified. Family 2 comprised of a total of 10 children with six affected siblings (4 girls and 2 boys) born to healthy consanguineous Saudi Arabian parents. Detailed extensive pedigree analysis confirmed that they were completely unrelated to Family 1. It was documented that 4 of the affected children (2 girls and 2 boys) had died previously due to lung disease (between the ages of 25 and 32). Both living sisters developed respiratory symptoms at an early age and pulmonary function test showed severe restriction. CT imaging (FIGS. 7A-7I) was very similar to Family 1. These patients also showed normal appearance, development and laboratory findings. Other known causes of fibrosis were excluded. One of the sisters underwent a lung transplant at age 27 and the second is currently on the waiting list. FIG. 2C describes Family 2.

Methods.

All samples were collected with Institutional Review Board approved written informed consents. The study was approved by the Research Advisory Council (RAC), King Faisal Specialist Hospital and Research Centre (KFSH&RC-RAC #2120 009).

Sequence Analysis.

Genomic DNA was extracted from whole blood or paraffin-embedded archived tissue of the three affected patients, their parents and 11 unaffected relatives (Family 1) using standard methods. Bi-directional sequencing of the coding regions of known IPF-associated genes (TERT, TERC, ABCA3 and SFTPB) was performed in patients and nuclear family members of Family 1A. Genomic DNA was extracted from whole blood from 2 affected patients and 3 unaffected family members of Family 2 using standard conditions. The full coding regions of S100A13 (NM 001024210) and S100A3 (NM 002960.1) were sequenced for all available members (affected and unaffected of Families 1B & 2) and 28 sporadic patients with PF, using standard PCR conditions. Sequence analysis was performed manually using the SeqMan 6.1 module of the Lasergene software package (DNA Star Inc. WI, USA).

Linkage Analysis and Homozygosity Mapping.

Linkage analysis was performed using the Allegro module of the easyLINKAGE initially on all the available members of Family 1A. This was followed by genotyping of all members using the Affymetrix Axiom® Genome-Wide CEU 1 Array platform analyzed by homozygosity mapping using AutoSNPa. Direct sequencing of candidate genes in the ROH, linkage interval and exome re-sequencing data of genomic DNA was performed using primer pairs designed to generate overlapping PCR amplicons of the entire coding region of each gene. A combined linkage analysis was later performed using the same methodology as above; with all available members of families 1A &1B and 2 (all affected individuals were included in this dataset).

Whole exome sequencing (WES) was first performed on the affected son of Family 1A using the Illumina® HiSeq2000 platform with TruSeqv3 chemistry by preparing and enriching the sample according to the manufacturer's standard protocol instructions. Concentration of each library was determined using Agilent's (Agilent Technologies, Santa Clara, CA, USA) QPCR NGS Library Quantification Kit (G4880A) and the sample was sequenced at a final concentration of 10 nM. Mapping and alignment was performed on read files (Fastq) generated from the sequencing platform via the manufacturer's proprietary software and using human genome (hg19/b37) using the Burrows-Wheeler Aligner (BWA) package, version 0.6.1. Further realignment and variant analysis were performed eventually determining SNP novelty against dbSNP (Human Build 135). Variants were annotated with gene and gene function from Ensembl (hypertext transfer protocol://_www.ensembl.org/index.html) and further analysis of possible causative variants by filtering the full exome dataset for all deletions, insertions, nonsense and canonical splice-site mutations, as well as missense mutations (with a PhyloP score of >3.5 of the underlying base change) were determined and reported. Similar WES analysis was performed later on one affected patient from both families 1B & 2 using the same methodology.

Immunofluorecence and Western Blotting.

Cells were lysed in Laemmli buffer, separated on either 7.5% SDS-PAGE (Bio-Rad, Hercules, CA), or 4-12% gradient SDS-PAGE gels and transferred onto PVDF membranes (Life Technologies, Carlsbad, CA) or Nitrocellulose membranes (Amersham Hybond ECL nitrocellulose membranes) and immunoblotted using primary rabbit antibodies against S100A3 (Santa Cruze, CA), S100A13, MMP2, MMP9, TIMP1, actin (Santa Cruze, CA) or GAPDH (Cell Signaling; Danvers, MA); followed by peroxidase-conjugated goat anti-rabbit IgG (Jackson ImmunoResearch Laboratories; West Grove, PA). Bands were visualized using chemiluminescence (SuperSignal West Pico, Thermo Scientific/Pierce, Rockford, IL) and exposed to X-ray film or scanned using ChemiDoc™ XRS+Molecular Imager with Image Lab™ software (Bio-Rad Laboratories, Inc. USA).

Sample Preparation for Label-Free Protein in-Solution Digestion.

Cells derived from patient and control samples were lysed using the RapiGest MS compatible lysis buffer (Waters, Manchester, UK). A total of 100 μg protein from whole cell lysate of each sample was subjected to proteome analysis by in-solution tryptic digestion. Briefly proteins were denatured in 0.1% RapiGest buffer at 80° C. for 15 minutes, reduced in 10 mM Dithiothreitol (DTT) at 60° C. for 30 min, and in 10 mM Iodoacetamide (IAA) (1.0 μL IAA/104) alkylation in the dark for 40 min at room temperature. Samples were trypsin-digested overnight at 37° C. and were diluted with aqueous 0.1% formic acid prior to LC/MS analysis. All samples were spiked with a known internal standard yeast alcohol dehydrogenase (ADH, P00330) at a concentration of 200 fmol per injection for absolute quantifications of all identified proteins using the Progenesis QI for proteomics V3.0 (Qlfp) (Nonlinear Dynamics/Waters).

Protein Identification, by LC-MSE SynaptG2 Platform.

The inventors used label-free quantitative 1-dimensional Nano Acquity liquid chromatography tandem mass spectrometry on Synapt G2 (Waters, Manchester, UK) and generated expression protein profiles between the sample groups. The instrument settings were optimized. Briefly, a mixture of 2 ng/μL Leucine Enkephalin and 500 fmol [Glu] 1-fibrinopeptide B in the same vial for the detector was set for mass (m/z) calibration respectively on the Mass Lynx IntelliStart (Waters, Manchester, UK) as described previously. All analyses were performed on Triazaic Nano source, and ionization in the positive ion mobility mode nanoESI (Waters, Manchester, UK). Data-independent acquisition (MSE)/iron mobility separation was performed and data acquired over a range of m/z 50-2000 Da using the Mass Lynx programs (version. 4.1, SCN833, Waters, Manchester, UK).

Expression Proteomics Data Analysis and Bioinformatics.

All data acquisitions were in triplicate runs with automated data processing and database search using the Uniprot Human specific protein sequence database on the Progenesis QI for proteomics for protein identification platform (Waters, UK and Nonlinear Dynamics, Newcastle, UK). Normalized protein abundance of significantly regulated proteins were considered (ANOVA; p<0.05), a fold change >1.5, and at false discovery rate (FDR) ~3%. The significant expression dataset was further evaluated for their functional/signaling pathway implications using the Ingenuity Pathway Analysis v8.7). (IPA) (Ingenuity Systems, www.ingenuity.com).

Quantitative Reverse Transcriptase-Polymerase Chain Reaction (qRT-PCR).

Total cellular RNA was isolated using TRIzol reagent (Ambion, Grand Island, NY), and complementary DNA was synthesized from 1-5 µg of RNA using a RT2 First Strand cDNA kit (Qiagen, Germantown, MD) according to the manufacturer's protocol. Primers for 18S rRNA were purchased from SA Biosciences/Qiagen (Valencia, CA). Primers for HA-tagged S100A3 (forward: 5' ctgtctctactgccacgagt (SEQ ID NO: 17); reverse: 5'-tcgtatgggtatgatccgcc (SEQ ID NO: 18)), endogenous S100A3 (forward: 5'-cccgaactggt-caactctca (SEQ ID NO: 5); reverse: 5'-gcctggcagagcttgtattt (SEQ ID NO: 6)), and plasmid backbone (forward: 5'-gtggcgctttctcatagctc (SEQ ID NO: 7); reverse: 5'-tgtct-taccgggttggactc (SEQ ID NO: 8)) were designed using PRIMER3. SABiosciences/Qiagen (Valencia, CA). qRT-PCR was performed on an Applied Biosystems StepOne Plus PCR system (Carlsbad, CA) using RT2 SYBR Green qRT-PCR Mastermix (SABiosciences) according to the manufacturer's directions. Collagen mRNA levels were normalized to 18S rRNA using the $2^{-\Delta\Delta Ct}$ method. For qRT-PCR of S100A3 in control and patient samples the following primers were used: (forward: 5'-ggacccgactgagtttcg (SEQ ID NO: 9); reverse: 5'-gctctgaggggcagtccttg (SEQ ID NO: 10)). For GAPDH the following primers were used (forward: 5'-caccatcttccaggagtgag (SEQ ID NO: 11); reverse: 5'-tcacgccacagtttcccgga (SEQ ID NO: 12)). For S100A13 in control and patient samples, the forward and reverse primers were, respectively, forward: 5'-CATCTGCT-CAAGGATGTGGG (SEQ ID NO: 19); and reverse: 5'-TCCTGATCTTCAGGTCTTT (SEQ ID NO: 20).

Intracellular Calcium and Mitochondrial Integrity Measurements.

Cytosolic calcium measurements were performed on patient or control fibroblasts (from unaffected donors) transfected with mutant-transcript of S100A3, patients fibroblasts transfected with wild-type S100A3 and control fibroblasts from unaffected individuals.

Mitochondrial calcium measurements were performed using Rhod-2 AM. Receptor mediated changes in intracellular fluorescence intensity in response to FGF-2 (Sigma USA, 10 ng/ml), bradykinin (Sigma USA, 50 µM) and ionomycin (Sigma USA, 2 µM) were followed using Zeiss LSM 510 META laser scanning confocal system (Carl Zeiss MicroImaging, GmbH, Germany). Mitochondrial staining was performed using Mito Tracker® Red CMXRos (Invitrogen™ Molecular Probes™, USA) (1 µM, 5 min at 37° C.) and viewed under Zeiss Yokogawa Spinning Disk confocal microscopy system (Carl Zeiss MicroImaging, GmbH, Germany).

Transmission Electron Microscopy (TEM) and Flow Cytometry.

For TEM, cells were fixed with 2.5% glutaraldehyde in cacodylate buffer (0.1 M, pH 7.4) for a minimum of 48 h. Osmication was performed using reduced osmium (1:1 mixture of 2% osmium tetroxide and 3% potassium ferrocyanide). After pre embedding in 1% agar, samples were dehydrated in ethanol series and embedded in epoxy resin. Thin sections (70 to 100 nm thickness) were collected on copper grids and contrasted with lead citrate. Imaging was performed using a transmission electron microscope operating at 300 kV (Titan Cryo Twin, FEI Company, Hillsboro, OR). Images were recorded on a 4k×4k CCD camera (Gatan Inc., Pleasanton, CA). For flow cytometry cells ($1\times10^6$ cells/ml) were labeled with Mito Tracker☐ Green FM (1 µM) for 45 min on ice, washed (PBS, pH 7.2), fixed in 1% paraformaldehyde, and analyzed by a BD FACSCalibur flow cytometer (BD Biosciences).

Statistical Analysis.

One way analysis of variance (ANOVA) was used to measure the overall difference among the means whereas unpaired two-tailed student t-test was used to measure the differences between groups. A p value of ≤0.05 was considered significant.

Identification of a Novel PF Region on Chromosome 1 (Using Families 1A&2).

Initial studies of bi-directional exonic sequencing of the candidate familial ILD-associated genes TERT, TERC, ABCA3 and SFTPB did not reveal any variations compared to normal reference sequences in patients from Family 1A. Subsequent genome-wide SNP microarray and linkage analysis identified a single peak with a multipoint LOD score of 2.95 corresponding to chromosome 1p12-q23.1. This was confirmed by homozygosity mapping, which corroborated a single ROH that was shared by all 3 affected patients and none of the unaffected family members and included 1579 SNP calls with identical genotypes between rs10802117 and rs1615480 (chr1:120,127,864-158,944,584 bp; base numbering is according to UCSC Genome Browser, build hg19) spanning approximately 38 Mb containing over 800 annotated genes. Three genes within this region, (MUC1, SMG5, and BCAN) were identified based on their similarity in function, expression, and/or protein family and type to previously identified familial ILD-associated genes. Sanger sequencing was performed for the three genes and were excluded as potential candidate familial ILD-causing genes. Further into the study, two affected sisters from Family 2 presenting with a remarkably similar clinical phenotype were similarly investigated and the resulting data combined with Family 1A.

Figure 2E:
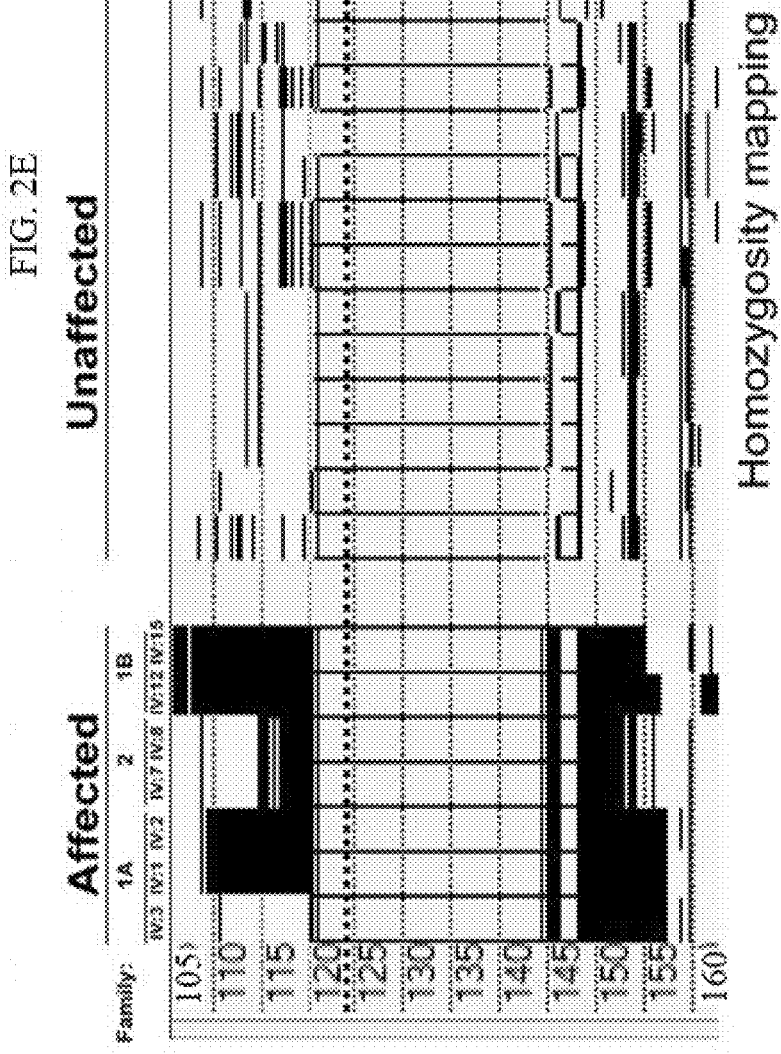
FIG. 2E shows a single ROH as a result of homozygosity mapping shared by all 7 affected patients between rs10802117 and rs11808053 confirming linkage analysis.
Figures 2I, 2J, 2K:
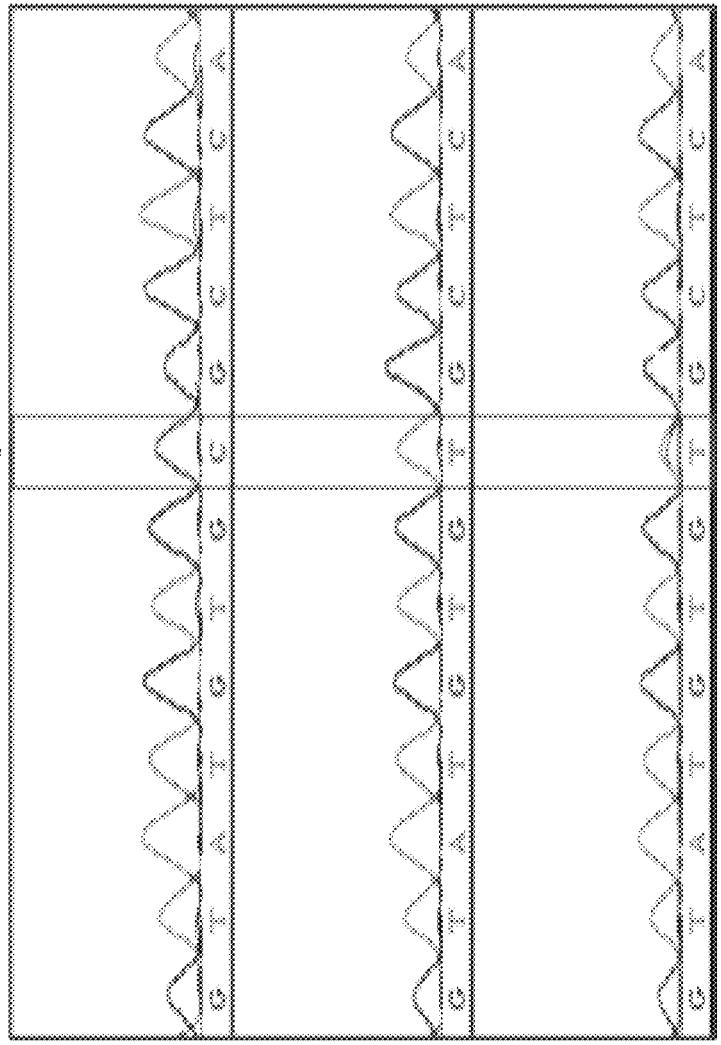
FIGS. 2I-2K respectively show the sequence chromatograms indicating the wild-type, homozygous affected and heterozygous carrier forms of the S100A3 protein (c.229C>T, p.R77C).

Homozygosity mapping reduced the critical interval to a 34 Mb region shared by all the 5 affected patients from both the families (FIG. 2E), defined proximally by rs10802117 and distally by rs11808053 (chr1:120,127,864-154,749,047 bp) containing over 363 annotated genes. Once enrolled, homozygosity mapping was also performed on the two affected living sisters from Family 1B (FIG. 2E) and although they shared the only common ROH, the critical region was unchanged. In addition, a total of 24 available unaffected family members showed no homozygosity for this region of interest (FIG. 2E). No other region of homozygosity was shared between all 7 affected on any other chromosome (Supplementary FIG. 1). The combined parametric multipoint linkage analysis using all three families revealed a single significant peak with a maximum LOD score of 5.28 corresponding to chromosome 1p12-q21.3 (FIG. 2B).

Exome Sequencing.

Initially, whole exome sequencing of all genes in the 31.3 Mbp linkage region was performed in the proband (Individual IV:1 FIG. 2A) of Family 1A. After filtering for homozygous non-synonymous SNVs that were either novel or had either low or unknown minor allele frequency in dbSNP, only 3 previously described variants were identified, rs3795737 in ISG20L2, rs143224912 in SETDB1, and rs138355706 in S100A3 and a novel variant in S100A13. Rs3795737 was excluded because it was found in the homozygous state throughout many different populations. Exonic sequencing of SETDB1, S100A3 and S100A13 was performed in all 3 affected and 6 unaffected family members. The rs143224912 variant in SETDB1 was excluded although it segregated with the disease phenotype, as it was present in 3% of the normal control population samples and due to a complete lack of conservation of the amino acid residue altered by the change throughout all orthologous species. Both of the variants, rs138355706 in S100A3 (229C>T, missense causing a p.R77C mutation) and a three base-pair deletion in S100A13 (c.238-241delATTG causing a frameshift p.I80Gfs*13) completely segregated with ILD (FIGS. 2F-2G). All 3 affected patients were homozygous for the two variants. Both parents were heterozygous for the variants and unaffected siblings and family members and an additional 7 unaffected extended family members were either heterozygous for the variants or were homozygous wild-type (FIGS. 2A-2C). Allele frequency for rs138355706 within the population was calculated from exome sequencing of 2000 individuals and was found to be 0.1% (Saudi Genome Project, unpublished data). Furthermore 500 ethnically-matched normal controls were genotyped for this change by re-sequencing of S100A3. Three of these individuals were heterozygous, but none was homozygous for rs138355706. Sequencing of the S100A3 intronic and 5' flanking sequences was performed in the affected patients and no other variants were identified. The novel truncating variant in S100A13 was not found in Saudi exome data (unpublished from the Saudi Human Genome Project), 1000G and ExAC databases. Later on in the study, whole exome sequencing was performed on one affected from both Families 1B & 2. Similarly as with the proband of Family 1A, only the variants in S100A3 and S100A13 survived filtration.

Haplotype Analysis.

Haplotype analysis was carried out using 8 markers (4 microsatellite markers flanking S100A3 and 3 further intragenic markers), and confirmed that the three affected individuals shared a specific disease haplotype on both chromosomes that was not present in the unaffected individuals (FIG. 8). Similar analysis demonstrated all 3 normal controls that were heterozygous for this change carry the disease haplotype on one chromosome and hence are related to the family therefore excluding them from the normal control set, providing additional support for the S100A3 p.R77C mutation in the pathogenesis of ILD in this family.

Sequencing of S100A3 and S100A13 in Family 1 & 2.

Further into this work, two affected sisters (4 other affected siblings had died previously) presenting with a remarkably similar clinical phenotype to the affected siblings of Family 1A were also recruited in the study. The entire coding regions of S100A3 and S100A13 were sequenced on the 2 affected patients, their parents and one unaffected brother. The patients were homozygous for the same c.229C>T (p.R77C) variant in S100A3 and c.238-241delATTG (p.I80Gfs*13) mutation and the remaining family members were heterozygous carriers for either change (FIGS. 2A-2C). In addition, molecular screening of the entire coding regions of S100A3 and S100A13 in all available members of Family 1B (enrolled last into the study) revealed that the affected patients were indeed the only individuals homozygous for c.229C>T (p.R77C) variant in S100A3 and c.238-241delATTG (p.I80Gfs*13) mutation and the additional unaffected were either heterozygous carriers or wild-type for the variations (FIGS. 2A-2C). Interestingly, all individuals in all three families that were heterozygous carriers for the truncating mutation in S100A13 were also heterozygous for c.229C>T (p.R77C) variant in S100A3, and all members that were wild-type normal were so for both lesions.

Consequences of the S100A3 c.229 C>T and S100A13 Variants.

The c.229 C>T variant resulted in an arginine to cysteine substitution at residue 77 within the second of the two EF-hand calcium-binding motifs in the 103 amino acid protein. The predicted consequences of this variant on protein structure/function was evaluated using the Polyphen-2 (ver. 2.2.2), SIFT prediction, and Combined Annotation Dependent Depletion (CADD) programs. Polyphen-2 and SIFT programs predicted minor effects of the mutation on protein structure/function with scores of 0.004 and 0.21, respectively, and a CADD PHRED score of 17.65.

Since microRNAs can modify translation efficiency by binding to coding sequence as well as 3'UTR sequence, we sought to determine whether the c.229 C>T mutation altered any known microRNA binding sites using MicroSNiPer (release 19) and a minimum 7-nucleotide seed sequence. We found no effect of the SNV on predicted microRNA binding sites moreover, analysis of predicted protease cleavage sites using PeptideCutter™ did not reveal any effect of the c.229 C>T mutation on protease cleavage sites in S100A3. Using MutationTaster, the inventors predict that the S100A13 variant should be "disease causing".

Effect of Mutations on S100A3 and S100A13 Expression.

Figure 3I:
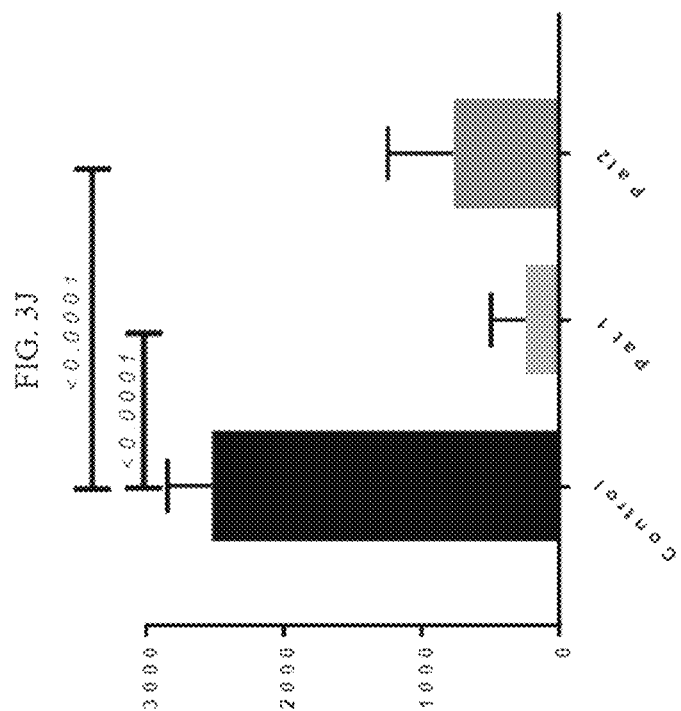
FIG. 3I. Relative protein expression of S100A3 in normal control and lung tissues from patients. Significantly reduced expression of S100A3 is seen in patient's lung tissues.
Figure 3I:
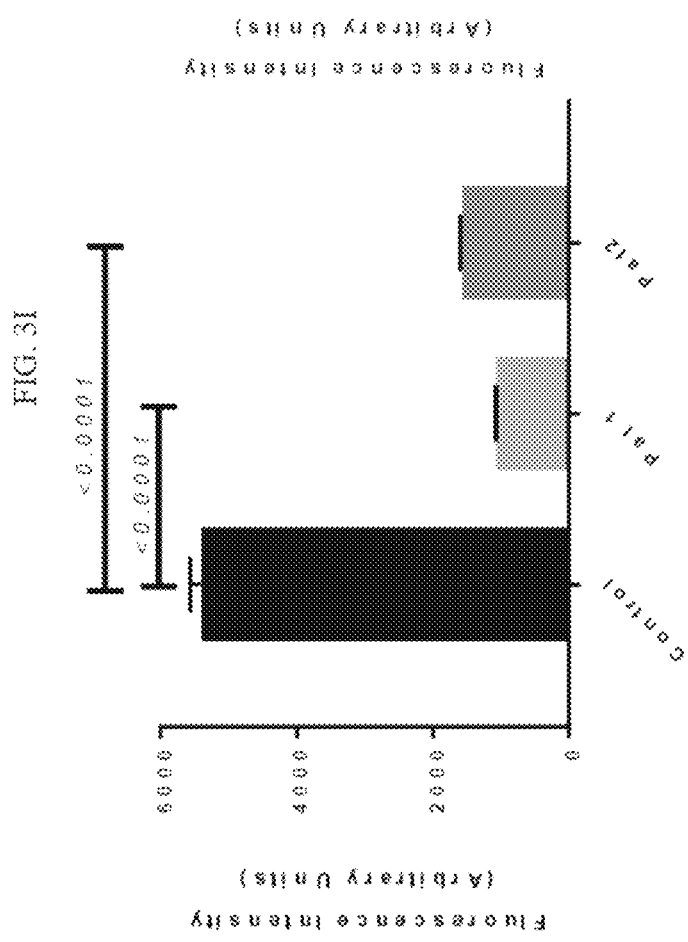
Figure 3Q:
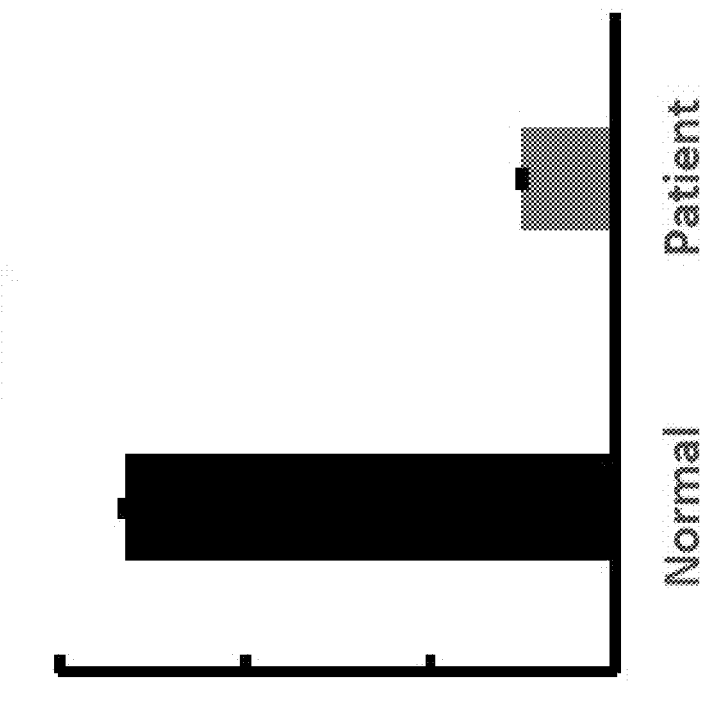
FIGS. 3Q and 3R, respectively depict S100A3 and S100A13 mRNA in normal and patient tissues as normalized to GAPDH mRNA. Relative mRNA expression of S100A3 and S100A13 in skin fibroblast isolated from normal control and patients. Data are representative of at least 3 independent experiments P-values are depicted on the horizontal bars.
Figure 3R:
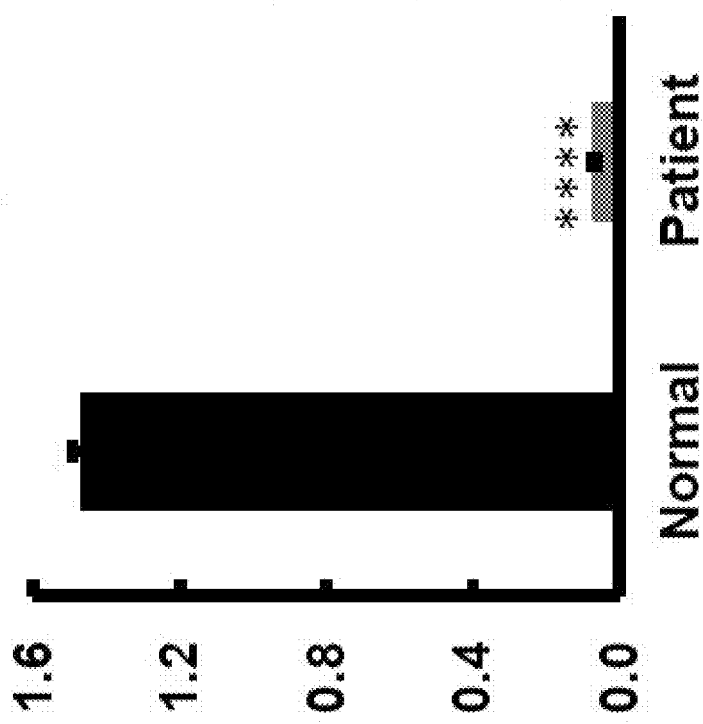

Indirect immunofluorescence staining of then slices obtained from healthy lung tissues demonstrated the presence of both proteins in healthy lung tissues (FIGS. 3A-3H and FIGS. 3I-3J). The staining was consistent with reports in The Human Protein Atlas demonstrating the expression of S100A3 in the lungs. (hypertext transfer protocol secure://_www.proteinatlas.org/ENSG00000188015-S100A3/tissue and hypertext transfer protocol secure://www.proteinatlas.org/ENSG00000189171-S100A13/tissue). Patients' lung tissues displayed a significantly reduced expression (FIGS. 3A-3H and FIGS. 3I-3J). Similar low expression levels were demonstrated in patient derived skin fibroblasts. Western blotting experiments demonstrated significantly reduced expression of S100A3 and S100A13 in skin fibroblasts isolated from patient cells compared to healthy controls (FIGS. 3K-3M and FIGS. 3N-3P). The reduced expression of the mutant proteins in patients was paralleled by reduced expression of mRNA levels of both variants compared to control (FIGS. 3Q-3R).

Effect of S100A3 and S100A13 Mutations on Intracellular Calcium Signaling and Mitochondrial Functions.

Since the S100A and S100A13 genes encode calcium-binding proteins, the possibility existed that the mutation may affect intracellular calcium homeostasis. In a series of experiments we measured intracellular calcium changes [Ca]i in response to bradykinin (50 μM) and fibroblast growth factor (FGF)-2 (10 ng/ml) in control and patient cells. The inventors found that receptor mediated calcium release was significantly reduced in patients compared to control fibroblast (FIGS. 4A and 4C). Maximum change following bradykinin stimulation was 2.34±0.07 and 1.47±0.14 fold increase in control and patient cells respectively ($p<0.0001$) (FIG. 4B). Similarly maximum change due to FGF-2 stimulation were 1.41±0.06 and 1.19±0.02 fold increase for control and patient cells, respectively ($p=0.017$) (FIG. 4D). A clear disparity in [Ca++]i changes between patient and control cells was further demonstrated by the levels of ionomycin-induced calcium release which were significantly higher in control compared to patient cells ($p<0.015$) (FIG. 4E). Since mitochondria accumulate calcium and shape the temporal and spatial calcium changes in many cell types and the inventors measured mitochondrial calcium changes in response to stimulation by bradykinin. It was found a significant difference in the intramitochondrial calcium changes as measured by Rhod2-AM fluorescence using confocal microscopy (FIG. 4F) (maximum response, $p=0.015$). Furthermore the inventors used Mito Tracker® Red CMXRos to map possible differences in mitochondrial morphology between control and patient cells.

Whereas control cells exhibited the "normal" distinct tubular shapes of mitochondria, patient cells exhibited more punctate fluorescence associated with aberrant mitochondrial morphology (FIGS. 5A-5D). In addition patient cells appear to have more mitochondrial staining than control cells (FIGS. 5A-5D). The latter was confirmed by flow cytometry experiments using Mitotracker Green FM labeled control and patient cells which demonstrated a significant increase in mitochondrial fluorescence intensity ($p=0.002$) in patients compared to control cells (FIG. 5E-5F). Transmission electron microscopy (TEM) showed evidence of mitochondrial damage, reduced cristae and reduced rough endoplasmic reticulum (RER) in patient samples compared to control (FIGS. 5G-5H).

Figure 5A:
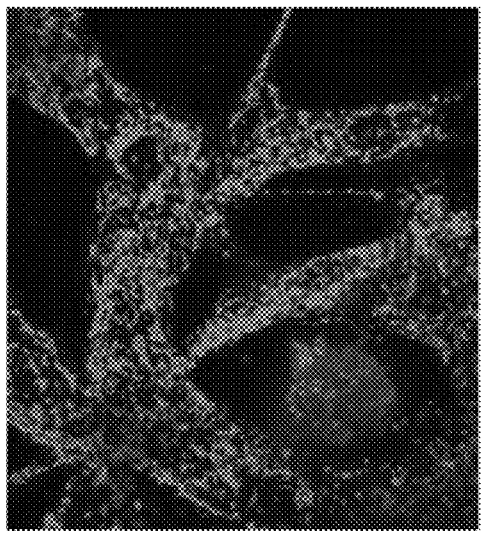
FIGS. 5A-5B, Confocal fluorescence micrographs of isolated normal/control skin fibroblasts labeled with Mito Tracker® Red CMXRos (2 µM) and the corresponding 3D intensity maps color coded so that warm colors indicate high intensity and cold colors indicate low intensity.
Figure 5C:
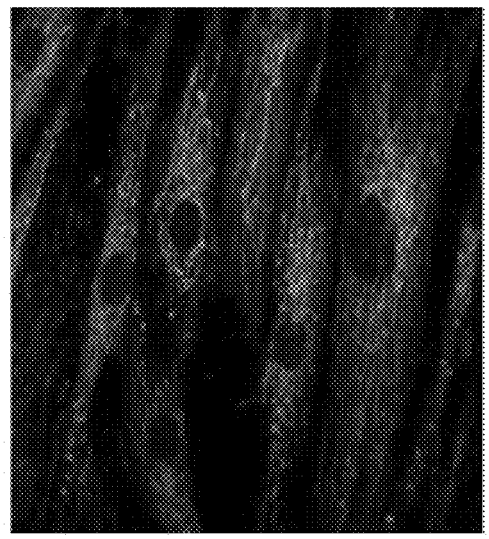
FIGS. 5C-5D, Confocal fluorescence micrographs of isolated patient skin fibroblasts labeled with Mito Tracker® Red CMXRos (2 µM) and the corresponding 3D intensity maps color coded so that warm colors indicate high intensity and cold colors indicate low intensity.
Figure 5B:
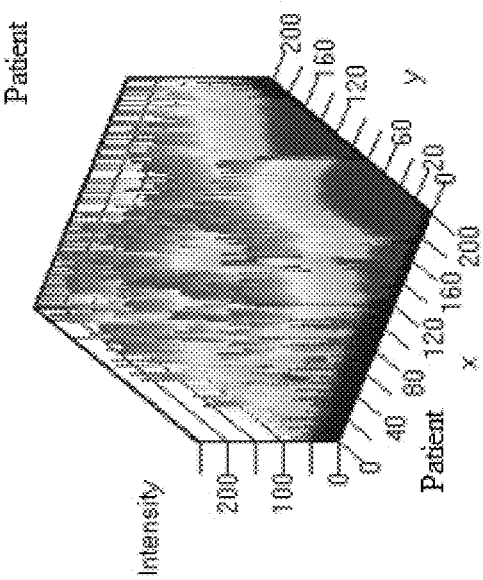
Figure 5D:
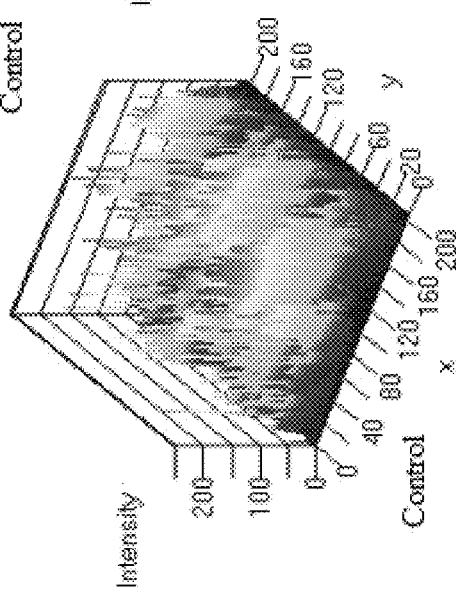
Figure 5I:
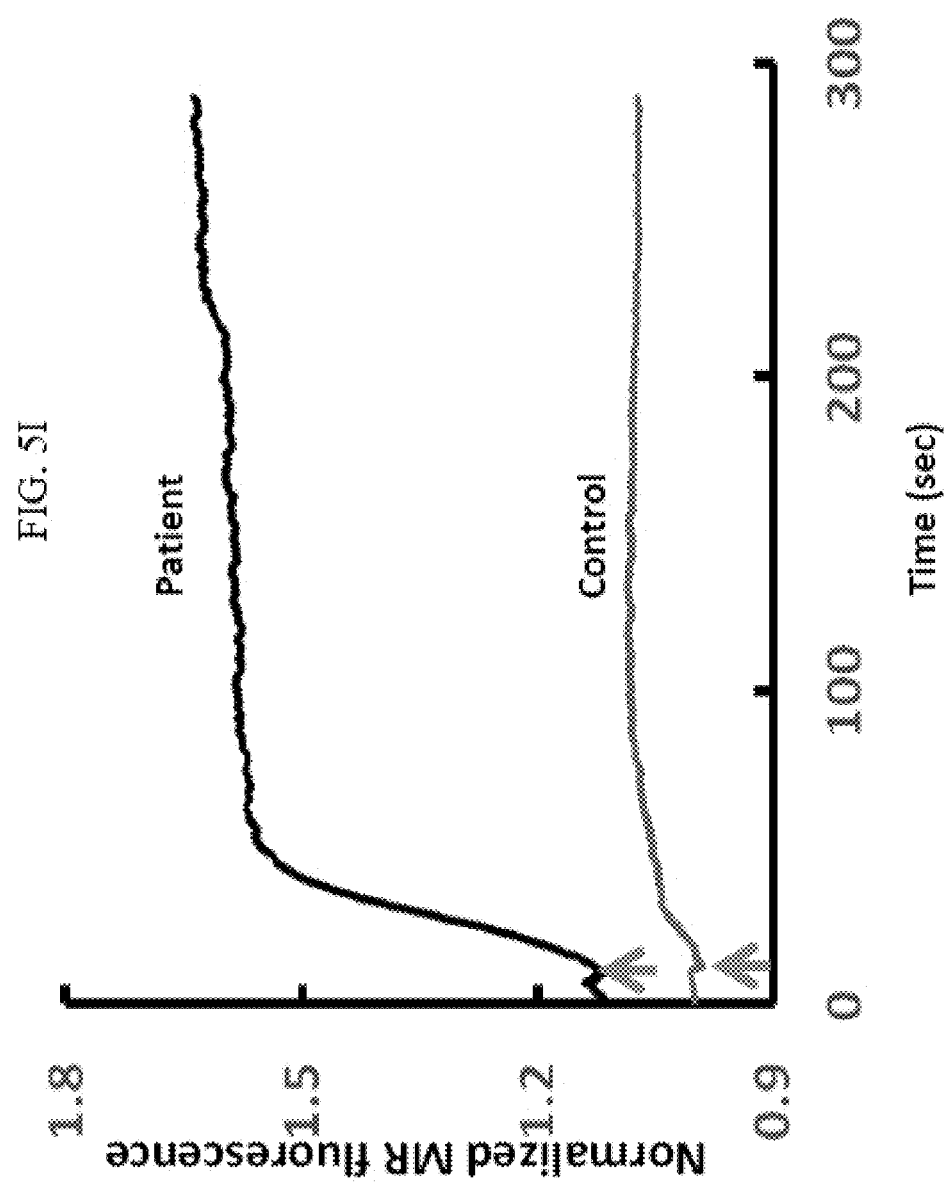
FIG. 5I. Effect of externally added oxidative insult ($H_2O_2$, 0.03%, arrow) on patients and control cells labeled with Mito Tracker Red CMXRos. Data are representative of three independent experiments.

The functional integrity of the mitochondria in both patient and control cells was further investigated by measuring the effect of external oxidative stress induced by treating the cells with hydrogen peroxide. FIG. 5I illustrates the ability of control cells to resist oxidative stress compared to patient cells.

Effect of S100A3 and S100A13 Mutation on Extracellular Matrix Remodeling.

Figure 6H:
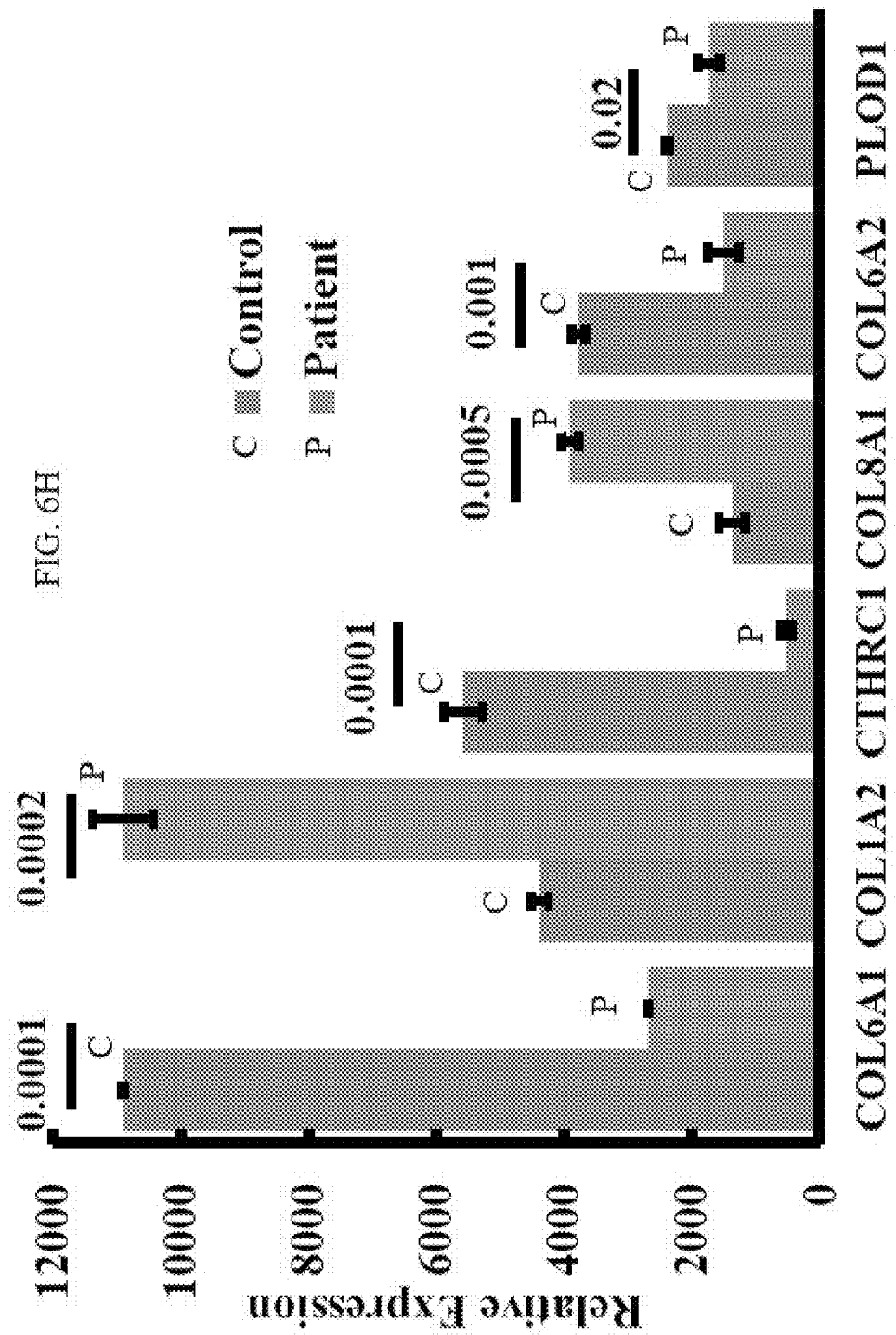
FIG. 6H: ECM associated proteins collagen alpha-1(VI) chain (COL6A1), collagen alpha-2(I) chain (COL1A2), collagen triple helix repeat-containing protein 1 (CTHRC1), collagen alpha-1(VIII) chain (COL8A1), collagen alpha-2 (VI) chain (COL6A2), and procollagen-lysine, 2-oxoglutarate 5-dioxygenase 1 (PLOD1).

Extracellular matrix (ECM) remodeling in the lungs is a hallmark of IPF. ECM was therefore investigated by measuring matrixins expression in patient and control fibroblasts. Western blot analysis demonstrated increased expression of two matrix metalloproteinases MMP2 and MMP9 in patients compared to control samples. Conversely tissue inhibitor of matrix metalloproteinase (TIMP)-1 expression was reduced in patient compared to control cells (FIGS. 6A-6F). Further analysis of ECM components in patient and control fibroblasts using proteomic approach with LC-MS demonstrated the increased expression of MMP1,3 and 14 (FIG. 6G). This was paralleled by differential expression of collagens I (COL1A2), collagen VI (COL6A1&2) collagen VIII (COL8A1), collagen triple helix repeat-containing protein 1 (CTHRC1) and procollagen-lysine, 2-oxoglutarate 5-dioxygenase 1 (PLOD1) (FIG. 6H).

Intracellular calcium is one of the most studied second messengers and its changes are coded by amplitude, frequency (oscillations) or both depending on the agonist, cell type, and chemical context. Appropriate intracellular calcium homeostasis is paramount to stimulus response coupling, in which engagement of cognate receptors evokes the "correct" cellular response. Cells receive many electrical, chemical and mechanical signals simultaneously and must therefore be able to assign the correct response to a particular agonist/antagonist. Inappropriate signaling or missignaling can lead to aberrant cellular behavior which underlies many diseases. The inventors have shown that the digeneic mutations were associated with aberrant calcium changes in response to two independent agonists bradykinin and FGF-2 suggesting a pivotal role for S100A3/S100A13 in receptor-induced calcium transients.

Central to receptor mediated calcium transients is mitochondrial calcium uptake which plays a crucial role in $[Ca^{2+}]i$ signaling by shaping and buffering calcium transients, regulating calcium influx and release and controlling mitochondrial functions. The inventors have shown that cells isolated from patients display increased numbers of mitochondria and an aberrant response to oxidative challenge with signs of autophagy, which may underpin the aberrant calcium response seen in the patient fibroblasts. Moreover, direct measurement of mitochondrial $Ca^{++}$ showed a significantly different response to bradykinin stimulation between patient and control fibroblasts.

Lungs from patients with IPF have increased levels of type I collagen content and their lung fibroblasts exhibit an increased capacity for type I collagen synthesis. Elevated levels of MMPs have been reported in blood and lung samples of IPF patients. Elevated levels of MMPs have also been shown to promote rather than inhibit fibrosis in a murine model of lung fibrosis. By combining Western blot and LC-MS analysis our study demonstrates elevated levels of MMP1, MMP2, MMP3, MMP9 and MMP14 and reduced levels of TIMP2 which were paralleled by differential expression of collagens and other ECM related proteins in cultured cells isolated from our patient.

There may be an association between short telomere length and pulmonary fibrosis and a short telomere length is one of the risk factors for IPF. Telomere length during cell division is controlled by telomerase reverse transcriptase (hTERT) and telomerase RNA component (TERC). Several mutations in TERT and TERC have been identified in IPF patients, however short telomeres have also been demonstrated in IPF patients without accompanying mutation in either TERT or TERC. It is possible that S100A3/A13 are involved in regulating the telomerase holoenzyme activity. While not being bound to any particular theory, the inventors believe that hTERT activity in the lungs may be regulated by S100A proteins and that low S100A3 or S100A13 expression may upregulate hTERT activity in the tested patients as they found elevated expression of MMP1,-2,-3,-9 and -14 in fibroblasts obtained from these patients.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. For example, the methods as disclosed which use S100A13 or S100A3, unless otherwise specified, also include the use of both S100A13 and S100A3.

As used herein, the term "and/or" includes any and all combinations of one or more of the associated listed items and may be abbreviated as "/".

Links are disabled by spelling out "http", by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5. The ranges specified herein include all intermediate values and subranges, thus a range of 1 to 10 includes 1, 2, 3, 4, 5, 6, 7, 8, 9 or 10 or a subrange of 1-3, 4-6 or 7-9.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page, or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for detecting pulmonary fibrosis in a human subject, comprising:
   detecting in a biological sample from the human subject a mutant S100A13 polynucleotide that comprises nucleotides 774 to 1046 of SEQ ID NO: 15, and
   administering a wild-type S100A13 protein of SEQ ID NO: 14 via a pulmonary route into the lungs of the human subject in which the mutant S100A13 has been detected and who has pulmonary fibrosis, and/or administering a drug that reduces inflammation or oxidative stress in the pulmonary system of the subject.

2. The method of claim 1, wherein the drug is an anti-inflammatory drug.

3. The method of claim 1, wherein the drug is a steroid drug.

4. The method of claim 1, wherein the drug reduces oxidative stress.

5. The method of claim 1, wherein the mutant polynucleotide encodes a mutant S100A13 protein that comprises the amino acid sequence of SEQ ID NO: 16.

6. The method of claim 1, further comprising:
   detecting in the biological sample a mutant S100A3 polynucleotide that comprises SEQ ID NO: 3.

7. The method of claim 6, wherein the mutant S100A3 polynucleotide encodes a mutant S100A3 protein that comprises SEQ ID NO: 4.

8. The method of claim 1, wherein a wild-type S100A13 protein is administered.

9. The method of claim 1, wherein a drug that reduces inflammation or oxidative stress is administered.

10. The method of claim 1, wherein said administering comprises administering a nucleic acid encoding the wild-type S100A13 protein into the circulatory system or circulatory system cells of the subject.

11. The method of claim 1, wherein said fibrosis is familial pulmonary fibrosis.

12. A method for detecting and treating pulmonary fibrosis in a human subject, comprising:
    detecting in a biological sample from the human subject a mutant S100A13 polynucleotide; and
    administering a wild-type S100A13 protein of SEQ ID NO: 14 via a pulmonary route into the lungs of the human subject; and/or
    administering a drug that reduces inflammation in the pulmonary system of the subject; and
    wherein said mutant S100A13 polynucleotide comprises nucleotides 774 to 1046 of SEQ ID NO: 15.

13. The method of claim 12, the wild-type S100A13 protein of SEQ ID NO: 14 is administered.

14. The method of claim 12, wherein said drug that reduces inflammation or oxidative stress is administered.

* * * * *

SEQUENCE LISTING

<160> NUMBER OF SEQ ID NOS: 20

<210> SEQ ID NO 1
<211> LENGTH: 738
<212> TYPE: DNA
<213> ORGANISM: Homo sapiens
<220> FEATURE:
<221> NAME/KEY: misc_feature

```
<222> LOCATION: (4)..(90)
<223> OTHER INFORMATION: Dimerization interface:
      order(4..20,26..28,37..38,40..42,70..73,75..76,78..81,
      83..90)
<220> FEATURE:
<221> NAME/KEY: misc_feature
<222> LOCATION: (20)..(74)
<223> OTHER INFORMATION: Ca2+ binding site: order (20,25,28,33..34,63,
      65,67,69,71,74)
<220> FEATURE:
<221> NAME/KEY: CDS
<222> LOCATION: (84)..(389)

<400> SEQUENCE: 1
agtctcagat tggtaaacac ccgaactggt caactctcaa gagaccatct ggttcaggtt        60
cctgactggg ccagcgagtg agg atg gcc agg cct ctg gag cag gcg gta gct      113
                         Met Ala Arg Pro Leu Glu Gln Ala Val Ala
                           1               5                  10 gcc atc gtg tgc acc ttc cag gaa tac gca ggg cgc tgt ggg gac aaa        161
Ala Ile Val Cys Thr Phe Gln Glu Tyr Ala Gly Arg Cys Gly Asp Lys
             15                  20                  25 tac aag ctc tgc cag gcg gag ctc aag gag ctg ctg cag aag gag ctg        209
Tyr Lys Leu Cys Gln Ala Glu Leu Lys Glu Leu Leu Gln Lys Glu Leu
         30                  35                  40 gcc acc tgg acc ccg act gag ttt cgg gaa tgt gac tac aac aaa ttc        257
Ala Thr Trp Thr Pro Thr Glu Phe Arg Glu Cys Asp Tyr Asn Lys Phe
     45                  50                  55 atg agt gtt ctg gac acc aac aag gac tgc gag gtg gac ttt gtg gag        305
Met Ser Val Leu Asp Thr Asn Lys Asp Cys Glu Val Asp Phe Val Glu
 60                  65                  70 tat gtg cgc tca ctt gcc tgc ctc tgt ctc tac tgc cac gag tac ttc        353
Tyr Val Arg Ser Leu Ala Cys Leu Cys Leu Tyr Cys His Glu Tyr Phe
 75                  80                  85                  90 aag gac tgc ccc tca gag ccc ccc tgc tcc cag tag cctctgctcc             399
Lys Asp Cys Pro Ser Glu Pro Pro Cys Ser Gln
                 95                 100 aggggggtgcg ctggctgtcg ggggctgggc atgtctccca caccccctcc taccctctct     459
cctgtacccc tttcaatctg gacttgccca ggtcttctgc gatcagttaa cccattttac     519
ctaggaggcc cagagatgtg agggctcctt cctcaggatg cccagcgaat gaggggtaga     579
gccactctgg ggcccagcct gcctgccgca ccctgtggc ctcccttgtg gatgggagga      639
ggcgggatct gctctgaggc cctcgaggct cagcagagcg tgcaccaatg agaccacgat     699
gggaaagggc ctatttaact cctaataaaa aactggcat                             738

<210> SEQ ID NO 2
<211> LENGTH: 101
<212> TYPE: PRT
<213> ORGANISM: Homo sapiens

<400> SEQUENCE: 2

Met Ala Arg Pro Leu Glu Gln Ala Val Ala Ala Ile Val Cys Thr Phe
  1               5                  10                  15

Gln Glu Tyr Ala Gly Arg Cys Gly Asp Lys Tyr Lys Leu Cys Gln Ala
             20                  25                  30

Glu Leu Lys Glu Leu Leu Gln Lys Glu Leu Ala Thr Trp Thr Pro Thr
         35                  40                  45

Glu Phe Arg Glu Cys Asp Tyr Asn Lys Phe Met Ser Val Leu Asp Thr
     50                  55                  60

Asn Lys Asp Cys Glu Val Asp Phe Val Glu Tyr Val Arg Ser Leu Ala
 65                  70                  75                  80
```

```
Cys Leu Cys Leu Tyr Cys His Glu Tyr Phe Lys Asp Cys Pro Ser Glu
            85                  90                  95

Pro Pro Cys Ser Gln
        100

<210> SEQ ID NO 3
<211> LENGTH: 720
<212> TYPE: DNA
<213> ORGANISM: Homo sapiens
<220> FEATURE:
<221> NAME/KEY: CDS
<222> LOCATION: (84)..(389)
<223> OTHER INFORMATION: Mutant rs138355706

<400> SEQUENCE: 3
agtctcagat tggtaaacac ccgaactggt caactctcaa gagaccatct ggttcaggtt      60
cctgactggg ccagcgagtg agg atg gcc agg cct ctg gag cag gcg gta gct    113
                         Met Ala Arg Pro Leu Glu Gln Ala Val Ala
                           1               5                  10 gcc atc gtg tgc acc ttc cag gaa tac gca ggg cgc tgt ggg gac aaa      161
Ala Ile Val Cys Thr Phe Gln Glu Tyr Ala Gly Arg Cys Gly Asp Lys
             15                  20                  25 tac aag ctc tgc cag gcg gag ctc aag gag ctg ctg cag aag gag ctg      209
Tyr Lys Leu Cys Gln Ala Glu Leu Lys Glu Leu Leu Gln Lys Glu Leu
         30                  35                  40 gcc acc tgg acc ccg act gag ttt cgg gaa tgt gac tac aac aaa ttc      257
Ala Thr Trp Thr Pro Thr Glu Phe Arg Glu Cys Asp Tyr Asn Lys Phe
 45                  50                  55 atg agt gtt ctg gac acc aac aag gac tgc gag gtg gac ttt gtg gag      305
Met Ser Val Leu Asp Thr Asn Lys Asp Cys Glu Val Asp Phe Val Glu
     60                  65                  70 tat gtg tgc tca ctt gcc tgc ctc tgt ctc tac tgc cac gag tac ttc      353
Tyr Val Cys Ser Leu Ala Cys Leu Cys Leu Tyr Cys His Glu Tyr Phe
 75                  80                  85                  90 aag gac tgc ccc tca gag ccc ccc tgc tcc cag tag cctctgctcc           399
Lys Asp Cys Pro Ser Glu Pro Pro Cys Ser Gln
             95                 100 aggggtgcg ctggctgtcg ggggctgggc atgtctccca cacccctcc taccctctct       459 cctgtacccc tttcaatctg gacttgccca ggtcttctgc gatcagttaa cccattttac     519
ctaggaggcc cagagatgtg agggctcctt cctcaggatg cccagcgaat gaggggtaga     579
gccactctgg ggcccagcct gcctgccgca ccctgtggc ctcccttgtg gatgggagga     639
ggcgggatct gctctgaggc cctcgaggct cagcagagcg tgcaccaatg agaccacgat     699
gggaaagggc ctatttaact c                                              720

<210> SEQ ID NO 4
<211> LENGTH: 101
<212> TYPE: PRT
<213> ORGANISM: Homo sapiens

<400> SEQUENCE: 4

Met Ala Arg Pro Leu Glu Gln Ala Val Ala Ala Ile Val Cys Thr Phe
1               5                  10                  15

Gln Glu Tyr Ala Gly Arg Cys Gly Asp Lys Tyr Lys Leu Cys Gln Ala
            20                  25                  30

Glu Leu Lys Glu Leu Leu Gln Lys Glu Leu Ala Thr Trp Thr Pro Thr
        35                  40                  45

Glu Phe Arg Glu Cys Asp Tyr Asn Lys Phe Met Ser Val Leu Asp Thr
```

```
            50                  55                  60
Asn Lys Asp Cys Glu Val Asp Phe Val Glu Tyr Val Cys Ser Leu Ala
 65                  70                  75                  80

Cys Leu Cys Leu Tyr Cys His Glu Tyr Phe Lys Asp Cys Pro Ser Glu
                 85                  90                  95

Pro Pro Cys Ser Gln
            100

<210> SEQ ID NO 5
<211> LENGTH: 20
<212> TYPE: DNA
<213> ORGANISM: Artificial Sequence
<220> FEATURE:
<223> OTHER INFORMATION: S100A3 forward primer

<400> SEQUENCE: 5
cccgaactgg tcaactctca                                          20

<210> SEQ ID NO 6
<211> LENGTH: 20
<212> TYPE: DNA
<213> ORGANISM: Artificial Sequence
<220> FEATURE:
<223> OTHER INFORMATION: S100A3 reverse primer

<400> SEQUENCE: 6
gcctggcaga gcttgtattt                                          20

<210> SEQ ID NO 7
<211> LENGTH: 20
<212> TYPE: DNA
<213> ORGANISM: Artificial Sequence
<220> FEATURE:
<223> OTHER INFORMATION: Plasmid backbone primer forward

<400> SEQUENCE: 7
gtggcgcttt ctcatagctc                                          20

<210> SEQ ID NO 8
<211> LENGTH: 20
<212> TYPE: DNA
<213> ORGANISM: Artificial Sequence
<220> FEATURE:
<223> OTHER INFORMATION: tgtcttaccggggttggactc

<400> SEQUENCE: 8
tgtcttaccg ggttggactc                                          20

<210> SEQ ID NO 9
<211> LENGTH: 19
<212> TYPE: DNA
<213> ORGANISM: Artificial Sequence
<220> FEATURE:
<223> OTHER INFORMATION: qRT-PCR forward primer

<400> SEQUENCE: 9
ggaccccgac tgagtttcg                                           19

<210> SEQ ID NO 10
<211> LENGTH: 20
<212> TYPE: DNA
<213> ORGANISM: Artificial Sequence
<220> FEATURE:
<223> OTHER INFORMATION: qRT-PCR reverse primer
```

<400> SEQUENCE: 10
gctctgaggg gcagtccttg                                              20

<210> SEQ ID NO 11
<211> LENGTH: 20
<212> TYPE: DNA
<213> ORGANISM: Artificial Sequence
<220> FEATURE:
<223> OTHER INFORMATION: GAPDH control primer forward

<400> SEQUENCE: 11
caccatcttc caggagtgag                                              20

<210> SEQ ID NO 12
<211> LENGTH: 20
<212> TYPE: DNA
<213> ORGANISM: Artificial Sequence
<220> FEATURE:
<223> OTHER INFORMATION: GAPDH control primer reverse

<400> SEQUENCE: 12
tcacgccaca gtttcccgga                                              20

<210> SEQ ID NO 13
<211> LENGTH: 1166
<212> TYPE: DNA
<213> ORGANISM: Homo sapiens
<220> FEATURE:
<221> NAME/KEY: CDS
<222> LOCATION: (774)..(1070)
<223> OTHER INFORMATION: Homo sapiens S100 calcium binding protein A13
      (S100A13), transcript variant 1, mRNA.  Version: NM_001024210.2

<400> SEQUENCE: 13
ctcactaccg aaactcaccg aaggaaacag acgccagtgc tcctcccggg gctgccacca      60
cggctccggc aggcgggccg gggaccggcc gaacctgagt tgacggtgga ggggctcggg     120
ttagctagat gggcggttgg ttagatgcgt aagcggtagt atgcgagctc agttcgttgt     180
tgctggttgg ctgtctagtc ggccgatccg tctgctcacc cggcctgccc tttcctgcct     240
ttcgtctgca gcggccgcca gctcctgctc ggtgtccaaa acaaaatggc cgccacgtcc     300
agtgcttgtc tgaccggcta aaatggcgtc tacgcaatta cgtcaggcgt cagatccgcg     360
cacgactaga gggcgggaaa gatttgagct acgcctgcgc agagttgaga agctgatgtc     420
tcctcgactt ccaactggaa ccttgaaccc ccacatttct ggaccttgag cattcctcaa     480
gtaggaagat gtaatgcacc ttgacctctt tctaaataag acacttcccc aaataagggg     540
agttgagagt gaacagtctt cacgtctcca cccacttcca gatcccagag gagacagaca     600
tcggatggct gttacctcct cctaaaatgt ctgcatttac ccagataatc ttccaatgga     660
aatccatggt tcaagtgcca cctcttcagg aaagccatct gacttcaatc aggtcagccc     720
tgacaaaggt cagctagccc cttgaggaca tcagctttgg cctcagggtc cta atg      776
                                                                 Met
                                                                  1 gca gca gaa cca ctg aca gag cta gag gag tcc att gag acc gtg gtc      824
Ala Ala Glu Pro Leu Thr Glu Leu Glu Glu Ser Ile Glu Thr Val Val
        5                  10                 15 acc acc ttc ttc acc ttt gca agg cag gag ggc cgg aag gat agc ctc      872
Thr Thr Phe Phe Thr Phe Ala Arg Gln Glu Gly Arg Lys Asp Ser Leu
     20                  25                 30 agc gtc aac gag ttc aaa gag ctg gtt acc cag cag ttg ccc cat ctg      920
Ser Val Asn Glu Phe Lys Glu Leu Val Thr Gln Gln Leu Pro His Leu

```
ctc aag gat gtg ggc tct ctt gat gag aag atg aag agc ttg gat gtg        968
Leu Lys Asp Val Gly Ser Leu Asp Glu Lys Met Lys Ser Leu Asp Val
 50                  55                  60                  65 aat cag gac tcg gag ctc aag ttc aat gag tac tgg aga ttg att ggg       1016
Asn Gln Asp Ser Glu Leu Lys Phe Asn Glu Tyr Trp Arg Leu Ile Gly
                 70                  75                  80 gag ctg gcc aag gaa atc agg aag aag aaa gac ctg aag atc agg aag       1064
Glu Leu Ala Lys Glu Ile Arg Lys Lys Lys Asp Leu Lys Ile Arg Lys
             85                  90                  95 aag taa agccgcctgg ctgagatggg gtgggcaggg cagagctgat cagggccgag        1120
Lys cagaaccgca ctcttcccaa ataaagcttc ctccttgaaa cacaaa                    1166

<210> SEQ ID NO 14
<211> LENGTH: 98
<212> TYPE: PRT
<213> ORGANISM: Homo sapiens

<400> SEQUENCE: 14

Met Ala Ala Glu Pro Leu Thr Glu Leu Glu Glu Ser Ile Glu Thr Val
 1               5                  10                  15

Val Thr Thr Phe Phe Thr Phe Ala Arg Gln Glu Gly Arg Lys Asp Ser
                 20                  25                  30

Leu Ser Val Asn Glu Phe Lys Glu Leu Val Thr Gln Gln Leu Pro His
             35                  40                  45

Leu Leu Lys Asp Val Gly Ser Leu Asp Glu Lys Met Lys Ser Leu Asp
 50                  55                  60

Val Asn Gln Asp Ser Glu Leu Lys Phe Asn Glu Tyr Trp Arg Leu Ile
 65                  70                  75                  80

Gly Glu Leu Ala Lys Glu Ile Arg Lys Lys Lys Asp Leu Lys Ile Arg
                 85                  90                  95

Lys Lys

<210> SEQ ID NO 15
<211> LENGTH: 1162
<212> TYPE: DNA
<213> ORGANISM: Homo sapiens
<220> FEATURE:
<221> NAME/KEY: CDS
<222> LOCATION: (774)..(1049)
<223> OTHER INFORMATION: S100A13 frameshift mutant c.238-241delATTG.
      Encodes p.I80Gfs*13.

<400> SEQUENCE: 15
ctcactaccg aaactcaccg aaggaaacag acgccagtgc tcctcccggg gctgccacca       60
cggctccggc aggcgggccg gggaccggcc gaacctgagt tgacggtgga ggggctcggg      120
ttagctagat gggcggttgg ttagatgcgt aagcggtagt atgcgagctc agttcgttgt      180
tgctggttgg ctgtctagtc ggccgatccg tctgctcacc cggcctgccc tttcctgcct      240
ttcgtctgca gcggccgcca gctcctgctc ggtgtccaaa acaaaatggc cgccacgtcc      300
agtgcttgtc tgaccggcta aaatggcgtc tacgcaatta cgtcaggcgt cagatccgcg      360
cacgactaga gggcgggaaa gatttgagct acgcctgcgc agagttgaga agctgatgtc      420
tcctcgactt ccaactggaa ccttgaaccc ccacatttct ggaccttgag cattcctcaa      480
gtaggaagat gtaatgcacc ttgacctctt tctaaataag acacttcccc aaataagggg      540
agttgagagt gaacagtctt cacgtctcca cccacttcca gatcccagag gagacagaca      600
```

```
tcggatggct gttacctcct cctaaaatgt ctgcatttac ccagataatc ttccaatgga      660
aatccatggt tcaagtgcca cctcttcagg aaagccatct gacttcaatc aggtcagccc      720
tgacaaaggt cagctagccc cttgaggaca tcagctttgg cctcagggtc cta atg        776
                                                         Met
                                                         1 gca gca gaa cca ctg aca gag cta gag gag tcc att gag acc gtg gtc       824
Ala Ala Glu Pro Leu Thr Glu Leu Glu Glu Ser Ile Glu Thr Val Val
            5                  10                  15 acc acc ttc ttc acc ttt gca agg cag gag ggc cgg aag gat agc ctc       872
Thr Thr Phe Phe Thr Phe Ala Arg Gln Glu Gly Arg Lys Asp Ser Leu
         20                  25                  30 agc gtc aac gag ttc aaa gag ctg gtt acc cag cag ttg ccc cat ctg       920
Ser Val Asn Glu Phe Lys Glu Leu Val Thr Gln Gln Leu Pro His Leu
     35                  40                  45 ctc aag gat gtg ggc tct ctt gat gag aag atg aag agc ttg gat gtg       968
Leu Lys Asp Val Gly Ser Leu Asp Glu Lys Met Lys Ser Leu Asp Val
 50                  55                  60                  65 aat cag gac tcg gag ctc aag ttc aat gag tac tgg aga ttg ggg agc      1016
Asn Gln Asp Ser Glu Leu Lys Phe Asn Glu Tyr Trp Arg Leu Gly Ser
                 70                  75                  80 tgg cca agg aaa tca gga aga aga aag acc tga agatcaggaa gaagtaaagc    1069
Trp Pro Arg Lys Ser Gly Arg Arg Lys Thr
                 85                  90 cgcctggctg agatggggtg ggcagggcag agctgatcag ggccgagcag aaccgcactc    1129
ttcccaaata agcttcctc cttgaaacac aaa                                  1162

<210> SEQ ID NO 16
<211> LENGTH: 91
<212> TYPE: PRT
<213> ORGANISM: Homo sapiens

<400> SEQUENCE: 16

Met Ala Ala Glu Pro Leu Thr Glu Leu Glu Glu Ser Ile Glu Thr Val
 1               5                  10                  15

Val Thr Thr Phe Phe Thr Phe Ala Arg Gln Glu Gly Arg Lys Asp Ser
             20                  25                  30

Leu Ser Val Asn Glu Phe Lys Glu Leu Val Thr Gln Gln Leu Pro His
         35                  40                  45

Leu Leu Lys Asp Val Gly Ser Leu Asp Glu Lys Met Lys Ser Leu Asp
     50                  55                  60

Val Asn Gln Asp Ser Glu Leu Lys Phe Asn Glu Tyr Trp Arg Leu Gly
 65                  70                  75                  80

Ser Trp Pro Arg Lys Ser Gly Arg Arg Lys Thr
                 85                  90

<210> SEQ ID NO 17
<211> LENGTH: 20
<212> TYPE: DNA
<213> ORGANISM: Artificial Sequence
<220> FEATURE:
<223> OTHER INFORMATION: HA-tagged S100A3 forward primer

<400> SEQUENCE: 17
ctgtctctac tgccacgagt                                                  20

<210> SEQ ID NO 18
<211> LENGTH: 20
<212> TYPE: DNA
```

```
<213> ORGANISM: Artificial Sequence
<220> FEATURE:
<223> OTHER INFORMATION: HA-tagged S100A3 reverse primer

<400> SEQUENCE: 18
tcgtatgggt atgatccgcc                                          20

<210> SEQ ID NO 19
<211> LENGTH: 20
<212> TYPE: DNA
<213> ORGANISM: Artificial Sequence
<220> FEATURE:
<223> OTHER INFORMATION: Forward primer for S100A13 polynucleotide

<400> SEQUENCE: 19
catctgctca aggatgtggg                                          20

<210> SEQ ID NO 20
<211> LENGTH: 19
<212> TYPE: DNA
<213> ORGANISM: Artificial Sequence
<220> FEATURE:
<223> OTHER INFORMATION: Reverse primer for S100A3 polynucleotide

<400> SEQUENCE: 20
tcctgatctt caggtcttt                                           19
```